(12) United States Patent
Mitsuhashi et al.

(10) Patent No.: US 7,838,239 B2
(45) Date of Patent: Nov. 23, 2010

(54) METHODS REGARDING ENHANCED T-CELL RECEPTOR-MEDIATED TUMOR NECROSIS FACTOR SUPERFAMILY MRNA EXPRESSION IN PERIPHERAL BLOOD LEUKOCYTES IN PATIENTS WITH CROHN'S DISEASE

(75) Inventors: Masato Mitsuhashi, Irvine, CA (US); Stephan R. Targan, Santa Monica, CA (US)

(73) Assignees: Hitachi Chemical Co., Ltd., Tokyo (JP); Hitachi Chemical Research Center, Inc., Irvine, CA (US); Cedars-Sinai Medical Center, Los Angeles, CA (US)

(*) Notice: Subject to any disclaimer, the term of this patent is extended or adjusted under 35 U.S.C. 154(b) by 0 days.

(21) Appl. No.: 12/296,425

(22) PCT Filed: Apr. 5, 2007

(86) PCT No.: PCT/US2007/008597

§ 371 (c)(1),
(2), (4) Date: Jun. 8, 2009

(87) PCT Pub. No.: WO2007/117611

PCT Pub. Date: Oct. 18, 2007

(65) Prior Publication Data

US 2009/0253133 A1 Oct. 8, 2009

Related U.S. Application Data

(60) Provisional application No. 60/790,354, filed on Apr. 7, 2006.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 4,880,548 | A | 11/1989 | Pall et al. |
| 4,925,572 | A | 5/1990 | Pall |
| 5,210,015 | A | 5/1993 | Gelfand et al. |
| 5,491,063 | A | 2/1996 | Fisher et al. |
| 5,683,698 | A | 11/1997 | Chavali et al. |
| 6,692,916 | B2 | 2/2004 | Bevilacqua et al. |
| 7,332,631 | B2 | 2/2008 | Hogarth et al. |
| 2001/0006789 | A1 | 7/2001 | Maino et al. |
| 2002/0006613 | A1 | 1/2002 | Shyjan et al. |
| 2002/0048566 | A1 | 4/2002 | El-Deiry et al. |
| 2002/0106684 | A1 | 8/2002 | Kopreski |
| 2003/0138781 | A1 | 7/2003 | Whitehead |
| 2003/0148345 | A1 | 8/2003 | Kopreski |
| 2004/0265864 | A1 | 12/2004 | Mitsuhashi |
| 2007/0196835 | A1 | 8/2007 | Bankaitis-Davis et al. |
| 2008/0206761 | A1 | 8/2008 | Mitsuhashi |

| 2008/0261207 | A1 | 10/2008 | Mitsuhashi |

FOREIGN PATENT DOCUMENTS

| EP | 1243274 A | 9/2002 |
| WO | WO 98/47004 | 10/1998 |
| WO | WO 00/76492 A | 12/2000 |
| WO | WO 03/040404 | 5/2003 |
| WO | WO 03/059333 A | 7/2003 |
| WO | WO03090694 | 11/2003 |
| WO | WO 03/099312 A | 12/2003 |
| WO | WO 2005/044792 A | 5/2005 |
| WO | WO 2005/115115 | 12/2005 |
| WO | WO 2006/110091 A | 10/2006 |
| WO | WO 2006/116721 A1 | 11/2006 |
| WO | 2008/106451 | 9/2008 |

OTHER PUBLICATIONS

European Patent Office, European Search Report, Mar. 6, 2009.
Aggarwal, B. B., et al., "The Role of TNF and Its Family Members in Inflammation and Cancer: Lessons from Gene Deletion," Curr. Drug Targets Inflamm. Allergy, vol. 1, No. 4, Dec. 2002, pp. 327-341.
Ames et al., "Are vitamin and mineral deficiencies a major cancer risk?" Nature, 2002, 2: 694-704.
Bush et al., Cancer Chemoresistance: The relationship Between P53 and Multidrug Transporters, Int J Cancer, 2002, vol. 98, pp. 323-330.
Cardullo, et al., Detection of Nucleic Acid Hybridization by Nonradiative Fluorescence Resonance Energy Transfer, Proc. Nat'l Acad. Sci., 1988, vol. 85, pp. 8790-8794, USA.
Chaudhary et al., Prediction of response to infliximab in Crohn's disease, Digestive and Liver Disease, 2005, vol. 37, Issue 8, pp. 559-563.
Chiaretti S et al., Gene expression profile of adult T-cell acute lymphocytic leukemia identifies distinct subsets of patients with different response to therapy and survival, Blood, Apr. 1, 2004, vol. 103, Issue 7, pp. 2771-2778.
Flores Mona G et al., In vitro evaluation of the effects of candidate immunosuppressive drugs: flow cytometry and quantitative real-time PCR as two independent and correlated read-outs, Journal of Immunological Methods, Jun. 2004, vol. 289, Issue 1-2, pp. 123-135.

(Continued)

*Primary Examiner*—Robert Landsman
(74) *Attorney, Agent, or Firm*—Knobbe Martens Olson & Bear LLP

(57) ABSTRACT

A method is disclosed for determining whether a human having Crohn's disease is likely to respond to a therapy targeting a TNFSF member or a cytokine by measuring the level of certain mRNAs in response to a stimulus. A method of evaluating the effectiveness of a Crohn's disease therapy in a human is also disclosed. Furthermore, a method of screening compounds for use in the treatment of Crohn's disease is disclosed. A method of monitoring the disease state over time in Crohn's disease patients is also disclosed.

13 Claims, 16 Drawing Sheets

OTHER PUBLICATIONS

Fujikado et al., Identification of arthritis related gene clusters by microarray analysis of two independent mouse models for rheumatoid arthritis, Arthritis Research and Therapy, 2006, vol. 8, pp. 1-13.

Ghosh et al., Anti-TNF therapy in Crohn's disease, Novartis Foundation Symposium, 2004, vol. 263, pp. 193-218.

Giacomelli et al., Combination therapy with cyclosporine and methotrexate in pateints with early rheumatoid arthritis soon inhibits TNF production without decreasing TNF mRNA level. An in vivo and in vitro study, Clinical and Experimental Rheumatology, 2002, vol. 20, pp. 365-372.

Haertel C et al., Dose-dependent Immunomodulatory Effects of Acetylsalicylic Acid and Indomethacin in Human Whole Blood: Potential Role of Cyclooxygenase-2 Inhibition, Scandinavian Journal Immunology, Oct. 2004, vol. 60, Issue 4, pp. 412-420.

Hess et al., The Hydroxylamine of sulfamethoxazole Synergizes with FK506 and Cyclosporin A, Inhibiting T-Cell Proliferation, The Journal of Pharmacology and Experimental Techniques, Dec. 1996, vol. 281, Issue 1, pp. 540-548.

Juhasz et al., Quantification of Chemotherapeuytic Target Gene mRNA Expression in Human Breast Cancer Biopsies: Comparison of Real-Time Reverse Transcription-PCR vs. Relative Quantification Reverse Transcription-PCR Utilizing DNA Sequencer Analysis of PCR Product, Journal of Clinical Laboratory Analysis, 2003, vol. 17, pp. 184-194.

Klein N J et al., Ex-Vivo Assessment of Candidate Anti-Inflammatory Agents in the Treatment of Gram Negative Sepsis, Immunology and Infectious Diseases, 1994, vol. 4, Issue 1, pp. 33-35.

Leung, S. Y., et al., "Expression Profiling Identifies Chemokine (C-C Motif) Ligand 18 as an Independent Prognostic Indicator in Gastric Cancer," Gastroenterology, vol. 127, No. 2, Aug. 2004, pp. 457-469.

Mascheretti et al., Pharmacogenetic investigation of the TNF/TNF-receptor system in patients with chronic active Crohn's disease treated with infliximab, The Pharmacogenomics Journal, 2002, vol. 2, Issue 2, pp. 127-136.

Mehmut et al., Fas Ligand and TNF-Related Apoptosis-Inducing Ligand Induction on Infiltrating Lymphocytes in Bladder Carcinoma by Bacillus Calmette-Guerin Treatment, Urologica Internatiol, 2005, vol. 75, pp. 88-87.

Plevy et al., A Role for TNF-α and Mucosal T Helper-1 Cytokines in the Pathogenesis of Crohn's Disease, The Journal of Immunology, 1997, vol. 159, Issue 12, pp. 6276-6282.

Rodriguez-Caballero et al., A new simple whole blood flow cytometry-based method for simultaneous identification of activated cells and quantitative evaluation of cytokines released during activation, Laboratory Investigation, 2004, vol. 84, pp. 1387-1398.

Schimanski, C. C., et al., "Effect of Chemokine Receptors CXCR4 and CCR7 on the Metastatic Behavior of Human Colorectal Cancer," Clinical Cancer Research, vol. 11, No. 5, Mar. 2005, pp. 1743-1750.

Shetty et al., Pharmacogenomics of Response to Anti-Tumor Necrosis Factor Therapy in Patients with Crohn's Disease, American Journal of Pharmacogenomics, 2002, vol. 2, Issue 4, pp. 215-221.

Sträter, J., et al., "Expression of TRAIL and TRAIL Receptors in Colon Carcinoma: TRAIL-R1 Is an Independent Prognostic Parameter," Clinical Cancer Research, vol. 8, No. 12, Dec. 2002, pp. 3734-3740.

Warzocha et al., Tumor Necrosis Factor Ligand-Receptor System Can Predict Treatment Outcome in Lymphoma Patients, Journal of Clinical Oncology, 1997, vol. 15, pp. 499-508.

Wouters et al., Inter- and intraindividual variation of endotoxin- and Beta(1->3)-glucan-induced cytokine responses in a whole blood assay, Toxicology and Industrial Health, 2002, vol. 18, pp. 15-27.

Younes, A., et al., "Clinical Implications of the Tumor Necrosis Factor Family in Benign and Malignant Hematologic Disorders," Cancer, vol. 98, No. 3, Aug. 2003, pp. 458-467.

Younes, A., et al., "Emerging Applications of the Tumor Necrosis Factor Family of Ligands and Receptors in Cancer Therapy," J. Clin. Oncol., vol. 21, No. 18, Sep. 2003, pp. 3526-3534.

Christoph Hartel et al., Delayed Cytokine mRNA Expression Kinetics after T-Lymphocyte Costimulation: A Quantitative Measure of the Efficacy of Cyclosporin A-based Immunosuppression, Clinical Chemistry, 2002, vol. 48, Issue 12, pp. 2225-2231.

Darryl See et al., Increased Tumor Necrosis Factor Alpha (TNF-alpha) and Natural Killer Cell (NK) Function Using an Integrative Approach in Late Stage Cancers, Immunological Investigations, 2002, vol. 31, Issue 2, pp. 137-153.

European Patent Office, EP Search Report for EP 06772657.0, HITACHI.072VPC, Dec. 2, 2008.

Hiroko Matsunaga, Application of differential display to identify genes for lung cancer detection in peripheral blood, Int. J. of Cancer, 2002, vol. 100, Issue 5, pp. 593-599.

Jamila K. Adam et al., Immune responses in cancer, Pharmacology & Therapeutics, 2003, vol. 99, pp. 113-132.

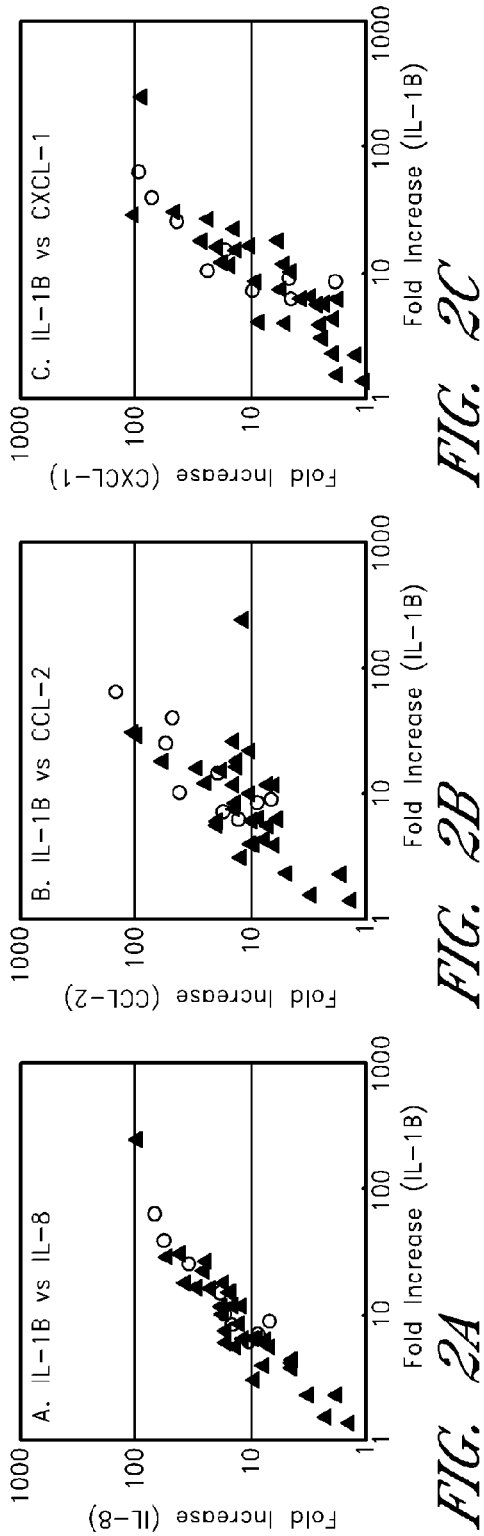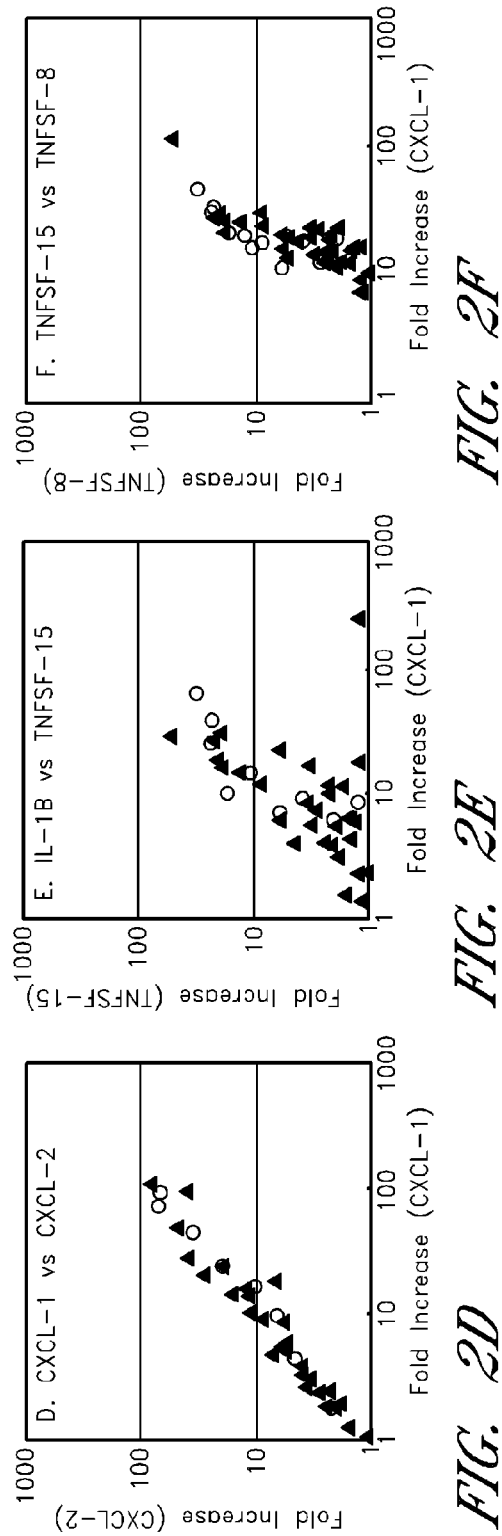

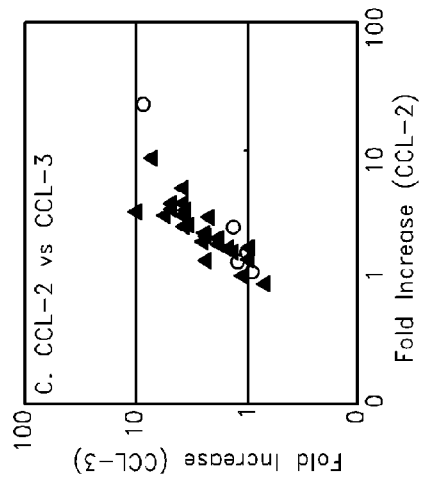
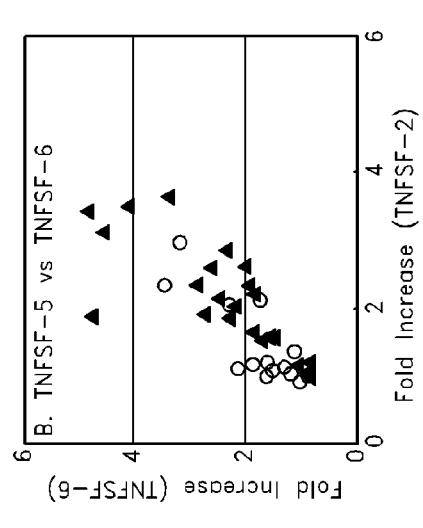
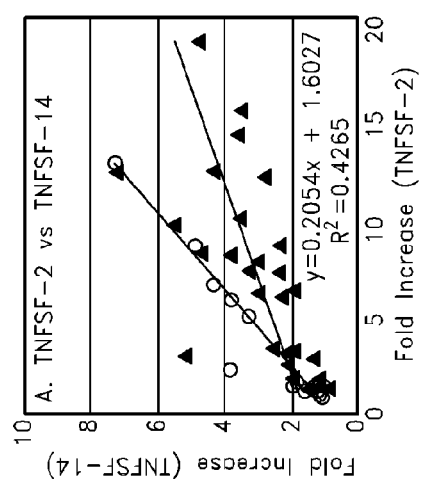
FIG. 3A  FIG. 3B  FIG. 3C
FIG. 3D  FIG. 3E  FIG. 3F

METHODS REGARDING ENHANCED T-CELL RECEPTOR-MEDIATED TUMOR NECROSIS FACTOR SUPERFAMILY MRNA EXPRESSION IN PERIPHERAL BLOOD LEUKOCYTES IN PATIENTS WITH CROHN'S DISEASE

This application is the national phase of PCT Application No. PCT/US2007/008597, filed Apr. 5, 2007, which claims priority to U.S. Provisional Patent Application No. 60/790,354, filed Apr. 7, 2006, now expired, titled ENHANCED T CELL RECEPTOR-MEDIATED TNF-A AND CHEMOKINE MRNA EXPRESSION IN PERIPHERAL BLOOD LEUKOCYTES IN PATIENTS WITH CROHN'S DISEASE, each of which is hereby incorporated by reference in its entirety and made part of this specification.

BACKGROUND

1. Field

The disclosure relates to a method for predicting patient responsiveness to Crohn's disease treatments involving antagonizing tumor necrosis factor-α ("TNF-α"), another tumor necrosis factor superfamily member, or a cytokine, and to a method of monitoring the effectiveness of such therapy. The disclosure also relates to a method for screening compounds for use in the treatment of Crohn's disease. The disclosure also relates to a method for monitoring the disease state in Crohn's disease patients.

2. Description of the Related Art

Autoimmune disease is characterized by production of either antibodies that react with host cells or immune effector T cells that are autoreactive. Autoantibodies are frequently identified in certain types of autoimmune disease, such as anti-acetylcholine receptor antibodies in myasthenia gravis and anti-DNA antibodies in systemic lupus erythematosus. However, such autoantibodies are not seen in many types of autoimmune disease. Moreover, autoantibodies are often detected among healthy individuals, but such antibodies do not induce autoimmune disease. Thus, beside autoantibodies, additional yet-to-be identified mechanisms are evidently involved in the pathogenesis of autoimmune disease.

Once autoantibodies bind to the target host cells, the complement cascade is thought to be activated to form the C5-9 membrane attack complex on the target cell membranes, which leads to the death of host cells (see Esser, Toxicology 87, 229 (1994)). By-product chemotactic factors, such as C3a, C4a, or C5a recruit more leukocytes to the lesion (see Hugli, Crit. Rev. Immunol. 1, 321 (1981)). Recruited leukocytes or naturally present leukocytes at the lesion recognize antibody-bound cells (immune complex) via Fc receptors ("FcR"). Once the FcR is cross-bridged by the immune complex, leukocytes release TNF-α (see Debets et al., J Immunol. 141, 1197 (1988)), which binds to specific receptors present on the surface of host cells, and induce apoptosis or cell damage (see Micheau et al., Cell 114, 181 (2003)). Activated FcR also initiates the release of chemotactic cytokines to recruit different subsets of leukocytes to the lesion (see Chantry et al., Eur. J. Immunol. 19, 189 (1989)). In addition to the FcR, T cell receptors ("TCR") on cytotoxic T cells may also recognize host cells, and an activated TCR functions in the same manner as cross-bridged FcR (see Brehm et al., J. Immunol. 175, 5043 (2005)). TCR function is well characterized in terms of antigen presentation with an interaction with major histocompatibility complex (MHC) molecules (see Isaacs et al., Inflamm. Bowel Dis. 11 Suppl 1, S3 (2005), and Garcia et al., Cell 122, 333 (2005)). Although the TCR-mediated cytotoxic function is not well characterized, it may be involved in cases where no autoantibody is identified, because immunoglobulins and the TCR are unique molecules which are capable of recognizing the specific structure of the target. This is an overall hypothesis of the molecular mechanism of autoimmune disease.

Crohn's disease ("CD") is an immune disease involving inflammation of the gastrointestinal tract. Although it is well characterized clinically, its pathogenesis is poorly understood. It is known, however, that the expression of TNF-α, also known as tumor necrosis factor superfamily member 2 ("TNFSF-2"), is increased in inflammatory bowel diseases such as CD. Although mild to moderate CD may be treated with 5-ASA agents such as sulfasalazine, glucocorticoids, or purine analogs such as azathioprine or 6-mercaptopurine, therapeutic options for severe CD cases refractory to standard therapies, such as the administration of cyclosporine, tacrolimus, or anti-inflammatory cytokines, are limited and of varying effect. Most CD patients will require at least one surgical intervention. Because the choice of therapeutic options depends on an assessment of the disease state in CD patients, it would be desirable to develop new methods of evaluating the disease state and monitoring the progression of the disease.

The development of infliximab (Remicade®), a chimeric mouse-human monoclonal antibody against TNF-α, has been a recent advance in the therapy of severe CD. However, only about 65% of patients will respond to this agent, and only about half of those patients will enter complete remission after repeated infusions of the antibody (typically, once every 8 weeks for 44 weeks). Because of the cost of the treatment, which can amount to tens of thousands of dollars per year, a method of quickly and easily assessing whether a CD patient would be a good candidate for infliximab therapy, and of assessing the effectiveness of infliximab therapy once treatment has begun, would be highly desirable. Furthermore, a method of rapidly screening new agents that could be of use in treating CD would be of great benefit in developing new therapies to complement or supplant existing therapies.

SUMMARY

In an embodiment, a method of determining whether a human having Crohn's disease is likely to respond to a therapy is provided that comprises: stimulating leukocytes in vitro in a first sample that comprises leukocytes from the human; after the stimulation, measuring the amount of an mRNA selected from the group consisting of tumor necrosis factor superfamily ("TNFSF")-2, TNFSF-5, TNFSF-6, TNFSF-14, chemokine (C-C motif) ligand ("CCL")-2, CCL-3, CCL-4, and chemokine (C-X-C motif) ligand ("CXCL")-10 in the first sample; stimulating leukocytes in vitro in a second sample comprising leukocytes from the human with a control stimulus; measuring the amount of the mRNA in the second sample after stimulation; and determining a ratio of the amount of the mRNA in the first sample to the amount of the mRNA in the second sample, wherein the human is likely to respond to the therapy if the ratio is about 1.7:1 or greater.

In a further aspect, stimulating leukocytes in the first sample comprises intermixing an anti-T cell receptor antibody with the first sample.

In a further aspect, stimulating leukocytes in the first sample comprises intermixing with the first sample an agent selected from the group consisting of phorbol myristate acetate (PMA), phytohemagglutinin (PHA), wheat germ agglutinin (WGA), concanavalin-A (ConA), lipopolysaccharides (LPS), jacalin, fucoidan, heat-aggregated IgE, heat-aggregated IgA, heat-aggregated IgG., and heat-aggregated IgM.

In a further aspect, at least one of the first and second samples comprises whole blood.

In a further aspect, the control stimulus comprises a purified control immunoglobulin.

In a further aspect, the therapy targets TNF-α activity.

In a further aspect, the therapy comprises administration of infliximab.

In a further aspect, the therapy comprises administration of an agent selected from the group consisting of cyclosporine A and tacrolimus.

In an embodiment, a method of evaluating the effectiveness of a Crohn's disease therapy in a human is provided that comprises: stimulating leukocytes in vitro in a first sample comprising leukocytes from the human; stimulating leukocytes in vitro in a second sample comprising leukocytes from the human with a control stimulus; measuring the amount of an mRNA selected from the group consisting of tumor necrosis factor superfamily ("TNFSF")-2, TNFSF-5, TNFSF-6, TNFSF-14, chemokine (C-C motif) ligand ("CCL")-2, CCL-3, CCL-4, and chemokine (C-X-C motif) ligand ("CXCL")-10 in the first and second samples after stimulation; calculating a first ratio of the amount of the mRNA in the first sample to the amount of the mRNA in the second sample; administering the therapy to the human; stimulating leukocytes in vitro in a third sample comprising leukocytes from the human obtained after the administration of therapy; stimulating leukocytes in vitro in a fourth sample comprising leukocytes from the human obtained after the administration of therapy with the control stimulus; measuring the level of the mRNA in the third and fourth samples after stimulation; calculating a second ratio of the amount of the mRNA in the third sample to the amount of the mRNA in the fourth sample; and comparing the first and second ratios, wherein a significant difference in the ratios is indicative of an effective therapy.

In a further aspect, stimulating leukocytes in the first and third samples comprises intermixing an anti-T cell receptor antibody with the sample.

In a further aspect, stimulating leukocytes in the first and third samples comprises intermixing with the sample an agent selected from the group consisting of phorbol myristate acetate (PMA), phytohemagglutinin (PHA), wheat germ agglutinin (WGA), concanavalin-A (ConA), lipopolysaccharides (LPS), jacalin, fucoidan, heat-aggregated IgE, heat-aggregated IgA, heat-aggregated IgG, and heat-aggregated IgM.

In a further aspect, the control stimulus comprises a purified control immunoglobulin.

In a further aspect, at least one of the first, second, third and fourth samples comprises whole blood.

In a further aspect, the significant difference in the ratios is that the second ratio is greater than the first ratio, and the therapy comprises inactivation of tumor necrosis factor alpha.

In a further aspect, the therapy comprises administration of infliximab.

In a further aspect, the significant difference in the ratios is that the first ratio is greater than the second ratio.

In a further aspect, the therapy comprises administration of an agent selected from the group consisting of cyclosporine A and tacrolimus.

In an embodiment, a method of identifying a putative agent for treating Crohn's disease is provided that comprises: obtaining first, second, third, and fourth samples comprising leukocytes from a human whose leukocytes demonstrate at least a 1.7-fold increase in the transcription of an mRNA selected from the group consisting of tumor necrosis factor superfamily ("TNFSF")-2, TNFSF-5, TNFSF-6, TNFSF-14, chemokine (C-C motif) ligand ("CCL")-2, CCL-3, CCL-4, and chemokine (C-X-C motif) ligand ("CXCL")-10 when exposed to an anti-T cell receptor antibody; stimulating leukocytes in vitro in the first sample; stimulating leukocytes in vitro in the second sample with a control stimulus; measuring the amount of the mRNA in the first and second samples after stimulation; calculating a first ratio of the amount of the mRNA in the first sample to the amount of the mRNA in the second sample; exposing the third and fourth samples to the agent; stimulating leukocytes in vitro in the third sample after the exposure; stimulating leukocytes in vitro in the fourth sample with the control stimulus after the exposure; measuring the level of the mRNA in the third and fourth samples after stimulation; calculating a second ratio of the amount of the mRNA in the third sample to the amount of the mRNA in the fourth sample; and comparing the first and second ratios, wherein a significant difference in the ratios is indicative of a putative agent.

In a further aspect, stimulating leukocytes in the first and third samples comprises intermixing an anti-T cell receptor antibody with the samples.

In a further aspect, stimulating leukocytes in the first and third samples comprises intermixing with the sample an agent selected from the group consisting of phorbol myristate acetate (PMA), phytohemagglutinin (PHA), wheat germ agglutinin (WGA), concanavalin-A (ConA), lipopolysaccharides (LPS), jacalin, fucoidan, heat-aggregated IgE, heat-aggregated IgA, heat-aggregated IgG, and heat-aggregated IgM.

In a further aspect, the control stimulus comprises a purified control immunoglobulin.

In a further aspect, at least one of the first, second, third, and fourth samples comprises whole blood.

In a further aspect, the significant difference in the ratios is that the first ratio is greater than the second ratio.

In an embodiment, a method of evaluating the state of Crohn's disease in a human is provided that comprises: stimulating leukocytes in vitro in a first sample that comprises leukocytes and is obtained at a first time from the human; after the stimulation, measuring the amount of an mRNA selected from the group consisting of tumor necrosis factor superfamily ("TNFSF")-2, TNFSF-5, TNFSF-6, TNFSF-14, chemokine (C-C motif) ligand ("CCL")-2, CCL-3, CCL-4, and chemokine (C-X-C motif) ligand ("CXCL")-10 in the first sample; stimulating leukocytes in vitro with a control stimulus in a second sample comprising leukocytes obtained from the human at the first time; measuring the amount of the mRNA in the second sample after stimulation; determining a first ratio of the amount of the mRNA in the first sample to the amount of the mRNA in the second sample; stimulating leukocytes in vitro in a third sample that comprises leukocytes and is obtained from the human at a second time that is subsequent to the first time; after the stimulation, measuring the amount of the mRNA in the third sample; stimulating leukocytes in vitro with a control stimulus in a fourth sample comprising leukocytes obtained from the human at the second time; measuring the amount of the mRNA in the fourth sample after stimulation; determining a second ratio of the amount of the mRNA in the third sample to the amount of the mRNA in the fourth sample; and comparing the first and second ratios, wherein a significant difference in the first and second ratios is indicative of a change in the disease state.

In a further aspect, stimulating leukocytes in the first and third samples comprises intermixing an anti-T cell receptor antibody with the sample.

In a further aspect, stimulating leukocytes in the first and third samples comprises intermixing with the sample an agent selected from the group consisting of phorbol myristate acetate (PMA), phytohemagglutinin (PHA), wheat germ agglutinin (WGA), concanavalin-A (ConA), lipopolysaccharides (LPS), jacalin, fucoidan, heat-aggregated IgE, heat-aggregated IgA, heat-aggregated IgG, and heat-aggregated IgM.

In a further aspect, the control stimulus comprises a purified control immunoglobulin.

In a further aspect, at least one of the first, second, third and fourth samples comprises whole blood.

In a further aspect, the significant difference in the ratios is that the second ratio is greater than the first ratio, and the change in disease state is a progression of the disease.

In a further aspect, the significant difference in the ratios is that the first ratio is greater than the second ratio, and the change in disease state is a regression of the disease.

BRIEF DESCRIPTION OF THE DRAWINGS

FIGS. 2A-2F show the correlation among various HAG-induced mRNA responses. FIG. 2A shows IL-1B vs. IL-8. FIG. 2B shows IL-1B vs. CCL-2. FIG. 2C shows IL-1B vs. CXCL-1. FIG. 2D shows CXCL-1 vs. CXCL-2. FIG. 2E shows IL-1B vs. TNFSF-15. FIG. 2F shows TNFSF-15 vs. TNFSF-8.

FIGS. 3A-3F show the correlation among various anti-TCR-induced mRNA responses. FIG. 3A shows TNFSF-2 vs TNFSF-14. FIG. 3B shows TNFSF-5 vs TNFSF-6. FIG. 3C shows CCL-2 vs CCL-3. FIG. 3D shows CCL-2 vs CCL-4. FIG. 3E shows CCL-2 vs CCL-20. FIG. 3F shows CCL-8 vs CXCL-10.

FIG. 4A shows the kinetics of the reaction. FIG. 4B shows the dose response.

FIG. 5A shows the dose response and kinetics of the stimulus. FIG. 5B shows the kinetics of the stimulus.

DETAILED DESCRIPTION OF THE PREFERRED EMBODIMENT

Figure 1:
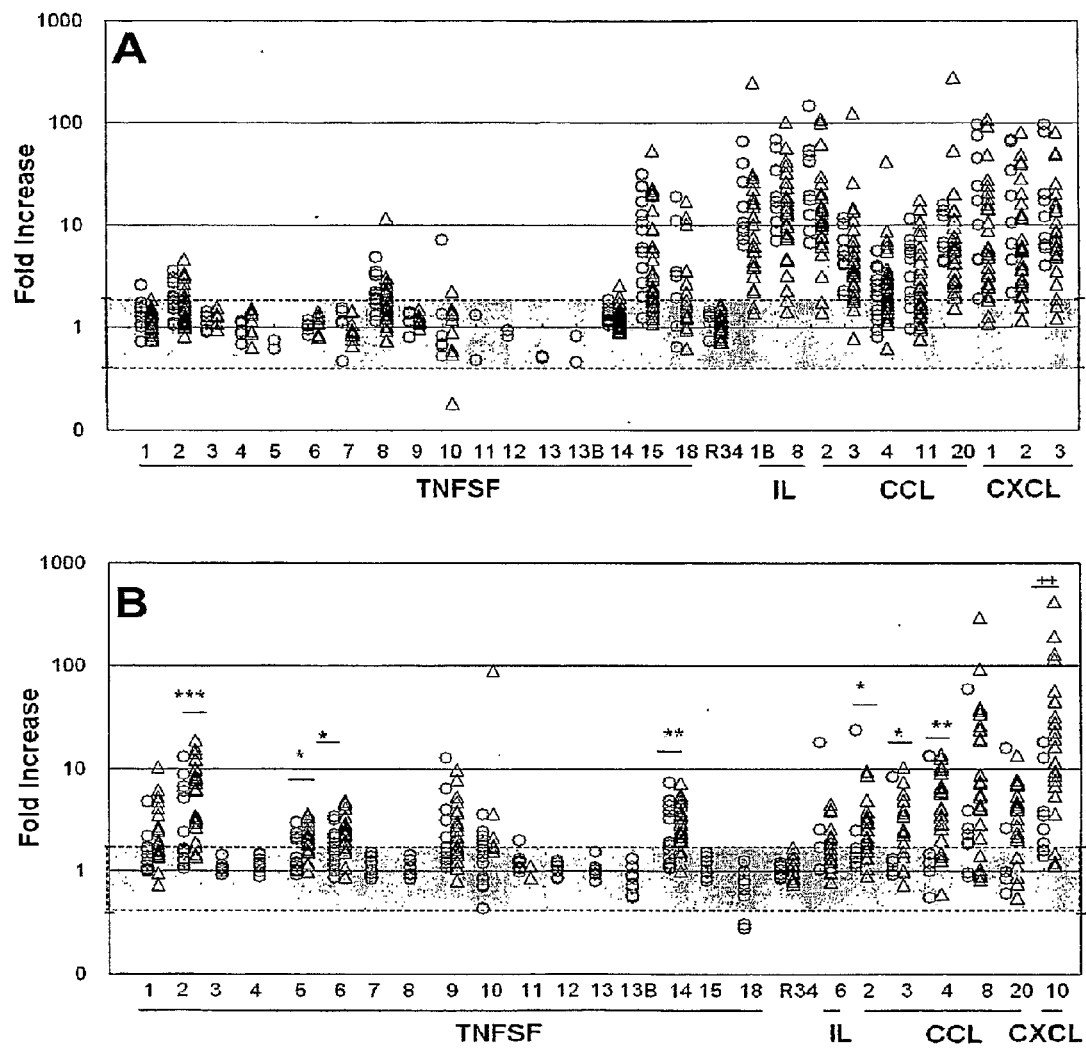
FIGS. 1A-1B show the results of a quantification of FcR and TCR-mediated gene expression of TNFSF, CCL, CXCL, and interleukin mRNA in human leukocytes in peripheral whole blood from CD patients (1A) and controls (1B).

The present disclosure relates to the use of differential mRNA transcription patterns in leukocytes in response to specific cellular stimuli in assessing whether CD patients are good candidates for specific therapies, such as therapy with Remicade®. The present disclosure also relates to the use of such differential transcription patterns in assessing whether therapy administered to a CD patient, such as therapy with Remicade®, is effective. The present disclosure also relates to the use of such differential transcription patterns in screening candidate agents for use in treating CD. The present disclosure also relates to the use of such differential transcription patterns in evaluating the state of CD in patients over time and monitoring the progression of the disease.

As described above, the pathology of CD may be related to the functioning of the FcR or TCR in the immune cells of a CD patient. In order to further assess the possible role of the FcR or the TCR in the disease, it is useful to assess whether the function of the FcR or TCR in circulating leukocytes in peripheral blood is normal before the leukocytes migrate to the pathological sites in patients with autoimmune disease, or is already enhanced before this migration. In order to analyze whether the function of the FcR or TCR is normal or enhanced in peripheral blood leukocytes in patients with CD, heat aggregated human IgG ("HAG") or monoclonal antibody against α/β T cell receptor ("anti-TCR") was added directly into heparinized whole blood in order to stimulate the FcR and TCR, respectively. Although multiple FcRs exist for IgG (FcγR), such as FcγRI, IIa, IIb, and III (GeneBank UniGene database), HAG acts as a universal stimulus that can react with all FcR subtypes. The changes in the mRNA level of members of the TNF superfamily (TNFSF) mRNA (see, for example, the GeneBank UniGene database) and selected CCL and CXCL chemokine mRNAs and chemotactic interleukin mRNAs (IL-1β, IL-6, and IL-8) resulting from the stimulus with HAG and anti-TCR were quantified. Because γ/δ anti-TCR did not induce any of the TNFSF mRNAs when mixed with whole blood, the α/β anti-TCR was used for the stimulus.

The method employed was as follows. Nucleotide sequences for various TNFSF and chemokine genes were retrieved from the UniGene database in the GenBank. PCR primers for each gene were designed by Primer Express (Applied Biosystem, Foster City, Calif.) and HYBsimulator (RNAture, Irvine, Calif.) (see Mitsuhashi et al., Nature 367: 759 (1994), and Hyndman et al., BioTechniques, 20:1090 (1996)) The sequences are summarized in Table I below. Oligonucleotides were synthesized by IDT (Coralville, 1A).

TABLE 1

| Target mRNA | Forward | Reverse |
|---|---|---|
| TNFSF-1 | CAGCTATCCACCCACACAGATG (SEQ ID NO: 1) | CGAAGGCTCCAAAGAAGACAGT (SEQ ID NO: 2) |
| TNFSF-2 | TCAATCGGCCCGACTATCTC (SEQ ID NO: 3) | CAGGGCAATGATCCCAAAGT (SEQ ID NO: 4) |
| TNFSF-3 | AGGGTGTACGTCAACATCAGTCA (SEQ ID NO: 5) | CACGGCCCCAAAGAAGGT (SEQ ID NO: 6) |
| TNFSF-4 | GCCCCTCTTCCAACTGAAGAA (SEQ ID NO: 7) | GGTATTGTCAGTGGTCACATTCAAG (SEQ ID NO: 8) |
| TNFSF-5 | CCACAGTTCCGCCAAACCT (SEQ ID NO: 9) | CACCTGGTTGCAATTCAAATACTC (SEQ ID NO: 10) |
| TNFSF-6 | TGGCAGCATCTTCACTTCTAAATG (SEQ ID NO: 11) | GAAATGAGTCCCCAAAACATCTCT (SEQ ID NO: 12) |
| TNFSF-7 | CACACTCTGCACCAACCTCACT (SEQ ID NO: 13) | TGCACTCCAAAGAAGGTCTCATC (SEQ ID NO: 14) |
| TNFSF-8 | ACCACCATATCAGTCAATGTGGAT (SEQ ID NO: 15) | GAAGATGGACAACACATTCTCAAGA (SEQ ID NO: 16) |
| TNFSF-9 | AGCTACAAAGAGGACACGAAGGA (SEQ ID NO: 17) | CGCAGCTCTAGTTGAAAGAAGACA (SEQ ID NO: 18) |
| TNFSF-10 | GGGAATATTTGAGCTTAAGGAAAATG (SEQ ID NO: 19) | AAAAGGCCCCGAAAAACTG (SEQ ID NO: 20) |
| TNFSF-11 | GAGTATCTTCAACTAATGGTGTACGTCACT (SEQ ID NO: 21) | TGGTGCTTCCTCCTTTCATCA (SEQ ID NO: 22) |
| TNFSF-12 | TACTGTCAGGTGCACTTTGATGAG (SEQ ID NO: 23) | GCAGTGGCTGAGAATTCCT (SEQ ID NO: 24) |
| TNFSF-13 | ATATGGTGTCCGAATCCAGGAT (SEQ ID NO: 25) | CCTGACCCATGGTGAAAGTCA (SEQ ID NO: 26) |
| TNFSF-13B | ATGCCTGAAACACTACCCAATAATT (SEQ ID NO: 27) | GCAAGTTGGAGTTCATCTCCTTCT (SEQ ID NO: 28) |
| TNFSF-14 | CGTCCGTGTGCTGGATGA (SEQ ID NO: 29) | CATGAAAGCCCCGAAGTAAGAC (SEQ ID NO: 30) |
| TNFSF-15 | TGCGAAGTAGGTAGCAACTGGTT (SEQ ID NO: 31) | CCATTAGCTTGTCCCCTTCTTG (SEQ ID NO: 32) |
| TNFSF-18 | CGGCTGTATAAAAACAAAGACATGAT (SEQ ID NO: 33) | TCCCCAACATGCAATTCATAAG (SEQ ID NO: 34) |
| IL-1B | GAAGATGGAAAAGCGATTTGTCTT (SEQ ID NO: 35) | GGGCATGTTTTCTGCTTGAGA (SEQ ID NO: 36) |
| IL-5 | GCTCTTGGAGCTGCCTACGT (SEQ ID NO: 37) | AAGGTCTCTTTCACCAATGCACTT (SEQ ID NO: 38) |
| IL-6 | TCATCACTGGTCTTTTGGAGTTTG (SEQ ID NO: 39) | TCTGCACAGCTCTGGCTTGT (SEQ ID NO: 40) |
| IL-8 | TGCTAAAGAACTTAGATGTCAGTGCAT (SEQ ID NO: 41) | TGGTCCACTCTCAATCACTCTCA (SEQ ID NO: 42) |
| IL-12A | GCAGGCCCTGAATTTCAACA (SEQ ID NO: 43) | GAAGTATGCAGAGCTTGATTTTAGTTTTA (SEQ ID NO: 44) |
| IL-12B | GAAGTATGCAGAGCTTGATTTTAGTTTTA (SEQ ID NO: 45) | CCCATTCGCT CCAAGATGAG (SEQ ID NO: 46) |
| IL-15 | TGAAGTGCTTTCTCTTGGAGTTACA (SEQ ID NO: 47) | CATTCCCATTAGAAGACAAACTGTTG (SEQ ID NO: 48) |
| IL-16C | AAAACCTCTTGGGAAGCATGAG (SEQ ID NO: 49) | GGGACCCCGAGGACAGTACT (SEQ ID NO: 50) |

TABLE 1-continued

Primer sequences

| Target mRNA | Forward | Reverse |
|---|---|---|
| CCL-2 | CCATTGTGGCCAAGGAGATC (SEQ ID NO: 51) | TGTCCAGGTGGTCCATGGA (SEQ ID NO: 52) |
| CCL-3 | CACAGAATTTCATAGCTGACTACTTTGA (SEQ ID NO: 53) | TCGCTTGGTTAGGAAGATGACA (SEQ ID NO: 54) |
| CCL-4 | GGTATTCCAAACCAAAAGAAGCA (SEQ ID NO: 55) | GTTCAGTTCCAGGTCATACACGTACT (SEQ ID NO: 56) |
| CCL-5 | AGTCGTCTTTGTCACCCGAAA (SEQ ID NO: 57) | AGCTCATCTCCAAAGAGTTGATGTAC (SEQ ID NO: 58) |
| CCL-7 | TGTGCTGACCCCACACAGA (SEQ ID NO: 59) | GCTTTGGAGTTTGGGTTTTCTTG (SEQ ID NO: 60) |
| CCL-8 | AGAGCTACACAAGAATCACCAACATC (SEQ ID NO: 61) | AGACCTCCTTGCCCCGTTT (SEQ ID NO: 62) |
| CCL-11 | CCCAGAAAGCTGTGATCTTCAA (SEQ ID NO: 63) | TCCTGCACCCACTTCTTCTTG (SEQ ID NO: 64) |
| CCL-13 | CCAAACTGGGCAAGGAGATCT (SEQ ID NO: 65) | GGCCCAGGTGTTTCATATAATTCT (SEQ ID NO: 66) |
| CCL-14 | TGCTTCACCTACACTACCTACAAGATC (SEQ ID NO: 67) | GACAATTCCGGGCTTGGA (SEQ ID NO: 68) |
| CCL-18 | CAGATTCCACAAAAGTTCATAGTTGAC (SEQ ID NO: 69) | CCGGCCTCTCTTGGTTAGG (SEQ ID NO: 70) |
| CCL-19 | CTGCTGTAGTGTTCACCACACTGA (SEQ ID NO: 71) | CTGCTGTAGTGTTCACCACACTGA (SEQ ID NO: 72) |
| CCL-20 | GATACACAGACCGTATTCTTCATCCTAA (SEQ ID NO: 73) | TGAAAGATGATAGCATTGATGTCACA (SEQ ID NO: 74) |
| CCL-21 | CGCTCTCAGGCAGAGCTATGT (SEQ ID NO: 75) | CTTGTCCAGATGCTGCATCAG (SEQ ID NO: 76) |
| CCL-22 | GCGCGTGGTGAAACACTTC (SEQ ID NO: 77) | ATCGGCACAGATCTCCTTATCC (SEQ ID NO: 78) |
| CCL-23 | CGAAGCATCCCGTGTTCACT (SEQ ID NO: 79) | GATGACACCCGGCTTGGA (SEQ ID NO: 80) |
| CCL-24 | CAGGAGTGATCTTCACCACCAA (SEQ ID NO: 81) | GGCGTCCAGGTTCTTCATGT (SEQ ID NO: 82) |
| CCL-25 | GGCGTCCAGGTTCTTCATGT (SEQ ID NO: 83) | GTAGAATATCGCAGCAGGCAGAT (SEQ ID NO: 84) |
| CCL-26 | CTGCTTCCAATACAGCCACAAG (SEQ ID NO: 85) | GAGCAGCTGTTACTGGTGAATTCA (SEQ ID NO: 86) |
| CCL-27 | CGTGCTTCACCTGGCTCAA (SEQ ID NO: 87) | GGTGCTCAAACCACTGTGACA (SEQ ID NO: 88) |
| CCL-28 | GGAAATGTTTGCCACAGGAAGA (SEQ ID NO: 89) | TGTTTCGTGTTTCCCCTGATG (SEQ ID NO: 90) |
| CXCL-1 | CCACTGCGCCCAAACC (SEQ ID NO: 91) | GCAGGATTGAGGCAAGCTTT (SEQ ID NO: 92) |
| CXCL-2 | CCCCTGGCCACTGAACTG (SEQ ID NO: 93) | TGGATGTTCTTGAGGTGAATTCC (SEQ ID NO: 94) |
| CXCL-3 | GGAATTCACCTCAAGAACATCCA (SEQ ID NO: 95) | GTGGCTATGACTTCGGTTTGG (SEQ ID NO: 96) |
| CXCL-4 | CCGTCCCAGGCACATCAC (SEQ ID NO: 97) | CCGTCCCAGGCACATCAC (SEQ ID NO: 98) |
| CXCL-5 | AGAGCTGCGTTGCGTTTGT (SEQ ID NO: 99) | TGGCGAACACTTGCAGATTACT (SEQ ID NO: 100) |

TABLE 1-continued

Primer sequences

| Target mRNA | Forward | Reverse |
|---|---|---|
| CXCL-6 | CAGAGCTGCGTTGCACTTGT (SEQ ID NO: 101) | ACACCTGCAGTTTACCAATCGTT (SEQ ID NO: 102) |
| CXCL-7 | TCTGGAATTCATCCCAAAAACA (SEQ ID NO: 103) | TCTGGAATTCATCCCAAAAACA (SEQ ID NO: 104) |
| CXCL-9 | CCACCTACAATCCTTGAAAGACCTT (SEQ ID NO: 105) | CAGTGTAGCAATGATTTCAATTTTCTC (SEQ ID NO: 106) |
| CXCL-10 | TCCACGTGTTGAGATCATTGC (SEQ ID NO: 107) | TCTTGATGGCCTTCGATTCTG (SEQ ID NO: 108) |
| CXCL-16 | CCCACAGCCAGGACATCAG (SEQ ID NO: 109) | CTTGCACAGCACATAGGAAAGG (SEQ ID NO: 110) |

Heat aggregated IgG (HAG) was prepared by heating 20 mg/mL human IgG (Sigma, St. Louis) in PBS at 63° C. for 15 min (see Ostreiko et al., Immunol Lett. 15, 311 (1987)). In 8-well strip microtubes, 1.2 µl of HAG or anti-TCR antibody (IgG1 κ) or controls (phosphate buffered saline for HAG or mouse control IgG1 κ for anti-TCR) (BioLegend, San Diego) were added, and stored at −20° C. until use. Although mouse IgG1 κ was employed as a control for anti-TCR antibody stimulation here, other purified control immunoglobulins could also be employed. Sixty µl of fresh heparinized whole blood was added into each well in triplicate, and incubated at 37° C. for 2-8 hours with cap closed. After each treatment, 50 µl of whole blood was transferred to filterplates as described below. Each blood sample was stored frozen at −80° C. until use.

The mRNA and cDNA were prepared from whole blood following the method set forth in Mitsuhashi et al., Clin. Chem. 52:4 (published as doi:10.1373/clinchem.2005.048983). The method disclosed in U.S. patent application Ser. No. 10/796,298, now U.S. Pat. No. 7,745,180, issued Jun. 29, 2010, which is incorporated here by reference, may also be employed. In brief, 96-well filterplates were placed over collection plates, and 150 µl 5 mM Tris, pH 7.4, was applied. Following centrifugation at 120×g for 1 min at 4° C., 50 µl of blood sample was applied to each well and immediately centrifuged at 120×g for 2 min at 4° C., followed by washing of each well with 300 µl PBS once with centrifugation at 2000×g for 5 min at 4° C. Then, 60 µl stock lysis buffer, supplemented with 1% 2-mercaptethanol (Bio Rad, Hercules, Calif., USA), 0.5 mg/ml proteinase K (Pierce, Rockford, Ill., USA), 0.1 mg/ml salmon sperm DNA (5 Prime Eppendorf/Brinkmann, Westbury, N.Y., USA), 0.1 mg/ml E. coli tRNA (Sigma), a cocktail of 10 mM each of specific reverse primers, and standard RNA34 oligonucleotides, were applied to the filterplates, followed by incubation at 37° C. for 10 min.

The filterplates were then placed over oligo(dT)-immobilized microplates (GENEPLATE®, RNAture) (see Mitsuhashi et al., Nature 357:519 (1992), and Hamaguchi et al., Clin. Chem. 44, 2256 (1998), both incorporated herein by reference), and centrifuged at 2000×g for 5 min at 4° C. Following overnight storage at 4° C., the microplates were washed with 100 µl plain lysis buffer 3 times, followed by 150 µl wash buffer (0.5 M NaCl, 10 mM Tris, pH 7.4, 1 mM EDTA) 3 times at 4° C. The cDNA was directly synthesized in each well by adding 30 µl buffer containing 1×RT-buffer, 1.25 mM each of dNTP, 4 units rRNasin, and 80 units of MMLV reverse transcriptase (Promega) (without primers), and incubation at 37° C. for 2 hours. The specific primer-primed cDNA existed in solution, and oligo(dT)-primed cDNA stayed immobilized in the microplate (see Hugli, Crit. Rev. Immunol. 1, 321 (1981)). For SYBR Green PCR (see Morrison et al., Biotechniques 24, 954 (1998), incorporated herein by reference), cDNA was diluted 4-fold in water, and 4 µl of cDNA solution was directly transferred to 384-well PCR plates, to which 5 µl iTaq SYBR master mix (BioRad, Hercules, Calif.) and 1 µl oligonucleotide cocktail (15 µM each of forward and reverse primer) were applied, and PCR was conducted in PRISM 7900HT (ABI), with one cycle of 95° C. for 10 min followed by 45 cycles of 95° C. for 30 sec and 60° C. for 1 min. TaqMan PCR could also be employed; in such a case, the cDNA solution is directly transferred to 384-well PCR plates, to which 5 µl of TaqMan universal master mix (ABI) and 1 µl oligonucleotide cocktail (15 µM each of forward and reverse primer, and 3-6 µM TaqMan probe) are applied, and PCR is conducted in PRISM 7900HT (ABI), with one cycle of 95° C. for 10 min followed by 45 cycles of 95° C. for 30 sec, 55° C. for 30 sec, and 60° C. for 1 min.

The 1×RT buffer was used as a negative control to confirm that no primer dimer was generated under SYBR Green PCR conditions. Moreover, the melting curve was analyzed in each case to confirm that the PCR signals were derived from the single PCR product. The Ct was determined by analytical software (SDS, ABI). The ΔCt was calculated by subtracting the Ct values of appropriate control samples, and the fold increase was calculated as $2^{(-\Delta Ct)}$, by assuming that the efficiency of each PCR cycle was 100%.

FIG. 1 shows the results of the analysis of the FcR and TCR-mediated gene expression of TNFSF, CCL, CXCL, and interleukin mRNA in human leukocytes in peripheral whole blood. The results are expressed in FIG. 1 as a fold increase over the control values. Responders were defined to be individuals showing a greater than 1.7-fold increase in mRNA level in response to the stimulus. In other embodiments, responders may also be defined as individuals showing a greater than 1.7-fold decrease in mRNA level when compared to a control stimulus. Each datum (○ for healthy adults and Δ for CD patients) was the mean from triplicate aliquots of whole blood. Blanket areas are the mean±3 standard deviation of the values of external control RNA34 (R34). The statistical significance shown in FIG. 1B (*: $p<0.05$, : $p<0.01$, *: $p<0.001$) was calculated by $\chi^2$ test using the population of responders and non-responders, as described above. ++ indicates p<0.01 by the t-test using the log values of the fold increase of the responder population only.

As shown in FIG. 1A, HAG mainly induced TNFSF-2, 8, 15, 18, IL-1B, 8, CCL-2, 3, 4, 11, 20, and CXCL-1, 2, 3, whereas anti-TCR induced different members of the TNFSF (TNFSF-1, 2, 5, 6, 9, 10, 14) and chemokine (IL-6, CCL-2, 3, 4, 8, 20, and CXCL-10) mRNAs. Further data obtained using whole blood of healthy individuals stimulated with HAG and expressed in terms of the cycle threshold (Ct) (see below), are shown in FIG. 13. Although CD patients did not show any enhancement in HAG-induced activities, the responder population (>1.7 fold increase) for anti-TCR-induced TNFSF-2, 5, 6, 14, and CCL-2, 3, and 4, was significantly larger in CD patients than in healthy controls. Interestingly, CD patients induced significantly (p<0.001) more TNFSF-2 (=TNFα) than TNFSF-14. These data suggest impairment of TCR function in peripheral blood leukocytes. This system will be useful in the analysis of cytotoxic functions of immune cells in CD and other autoimmune diseases.

FIG. 2 shows the correlation among various HAG-induced mRNA responses. In FIG. 2, the data from FIG. 1A were transformed to x-y plots. FIG. 2A shows IL-1B vs IL-8; FIG. 2B shows IL-1B vs CCL-2; FIG. 2C shows IL-1B vs CXCL-1; FIG. 2D shows CXCL-1 vs CXCL-2; FIG. 2E shows IL-1B vs TNFSF-15; and FIG. 2F shows TNFSF-15 vs TNFSF-8, respectively. In the Figure, o: healthy adults, ▲: CD.

FIG. 3 shows the correlation among various anti-TCR-induced mRNA responses. In FIG. 3, the data from FIG. 1A were transformed to x-y plots. FIG. 3A shows TNFSF-2 vs TNFSF-14; FIG. 3B shows TNFSF-5 vs TNFSF-6; FIG. 3C shows CCL-2 vs CCL-3; FIG. 3D shows CCL-2 vs CCL-4; FIG. 3E shows CCL-2 vs CCL-20; and FIG. 3F shows CCL-8 vs CXCL-10, respectively. In the Figure, o: healthy adults, ▲: CD. In FIG. 3A, regression lines for both control and CD patients were drawn.

Because of wide individual-to-individual variation, and the presence of the population of responders and non-responders, a standard Student's t-test is not appropriate for the analysis of these results. The responder populations (>1.7 fold increase, as noted above) for TNFSF-2, 5, 6, 14, CCL-2, 3, and 4 in CD patients were 92.9%, 66.7%, 75.0%, 82.1%, 75.0%, 75.0%, and 83.3%, respectively, which were significantly higher than that for healthy controls (38.9%, 28.6%, 42.9%, 44.4%, 33.3%, 20.0%, and 20.0%, respectively) by $\chi^2$ test (see FIG. 1B: *). When the fold increase of the responder population was compared in log scale, CD patients showed significantly (P<0.01) higher values than control subjects (see FIG. 1B: ++). Moreover, similar to the results of HAG-induced gene expression (FIG. 2), responders for certain TNFSF members and chemokines were also responders for other TNFSF members and chemokines (FIG. 3), suggesting that the variation in the anti-TCR data is derived from individual responses and not assay techniques. Surprisingly, the correlation between anti-TCR-induced TNFSF-2 (=TNFα) and TNFSF-14 was significantly (p<0.001) different between healthy control and CD patients: CD patients induced more TNFSF-2 than TNFSF-14, although these 2 TNFSF responses were correlated with each other in both cases (FIG. 3A).

External control RNA34 was unchanged in all cases, suggesting that the assay was performed appropriately. Although the results showed wide individual-to-individual variation, responders to certain TNFSF and chemokines (see FIG. 2), were also responders to other TNFSF and chemokines (see FIG. 2), suggesting that the variation of the data was derived from individual responses rather than the assay techniques. Interestingly, CD patients did not show any enhancement in HAG-induced activity, and some CD patients actually showed reduced activity in HAG-induced IL-1B, IL-8, CCL-20, and CXCL-3 mRNA expression (FIG. 1A). In contrast, anti-TCR induced different TNFSF (TNFSF-1, 2, 5, 6, 9, 10, 14) and chemokine (IL-6, CCL-2, 3, 4, 8, 20, and CXCL-10) mRNAs. IL-1B and IL-8 mRNA were not induced by anti-TCR.

Figure 4:
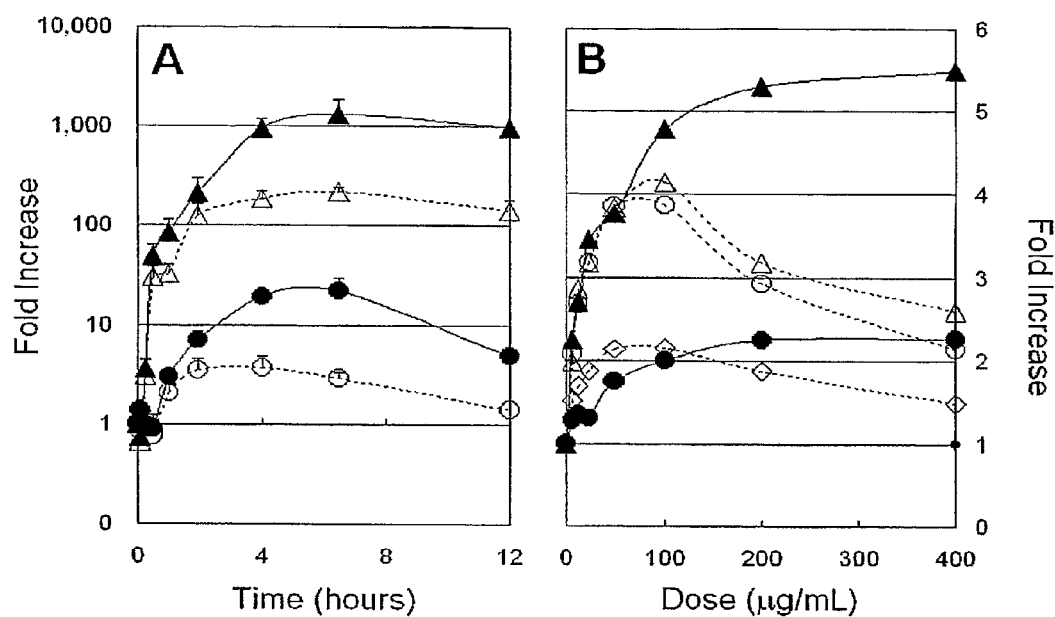
FIGS. 4A-4B show the effect of heat aggregated IgG (HAG) on TNFSF and chemokine mRNA expression in peripheral blood leukocytes.

Dose responses and kinetic studies for the HAG stimulation are shown in FIG. 4. FIG. 4 shows the effect of heat aggregated IgG (HAG) on TNFSF and chemokine mRNA expression in peripheral blood leukocytes. FIG. 4A shows the kinetics of the reaction. Triplicate aliquots of 60 μl each of heparinized whole blood was mixed with PBS (o, Δ), or 200 μg/mL HAG (●, ▲) and incubated at 37° C. for 0-12 hours. TNFSF-15 (o, ●) and IL-8 (Δ, ▲) mRNA were then quantified as described above. The fold increase was calculated using the values at time=0 as a control. FIG. 4B shows the dose response. Triplicate aliquots of 60 μl each of heparinized whole blood were mixed with various concentrations of HAG and incubated at 37° C. for 2 hours. TNFSF-2 (●), TNFSF-15 (▲), IL-8 (o), IL-1B (◇), and CXCL-2 (Δ) mRNA were then quantified as described above. The fold increase was calculated using the values for the solvent (PBS) as a control. Each data point was the mean±standard deviation (A) or mean (B) from triplicate aliquots of whole blood.

Figure 5:
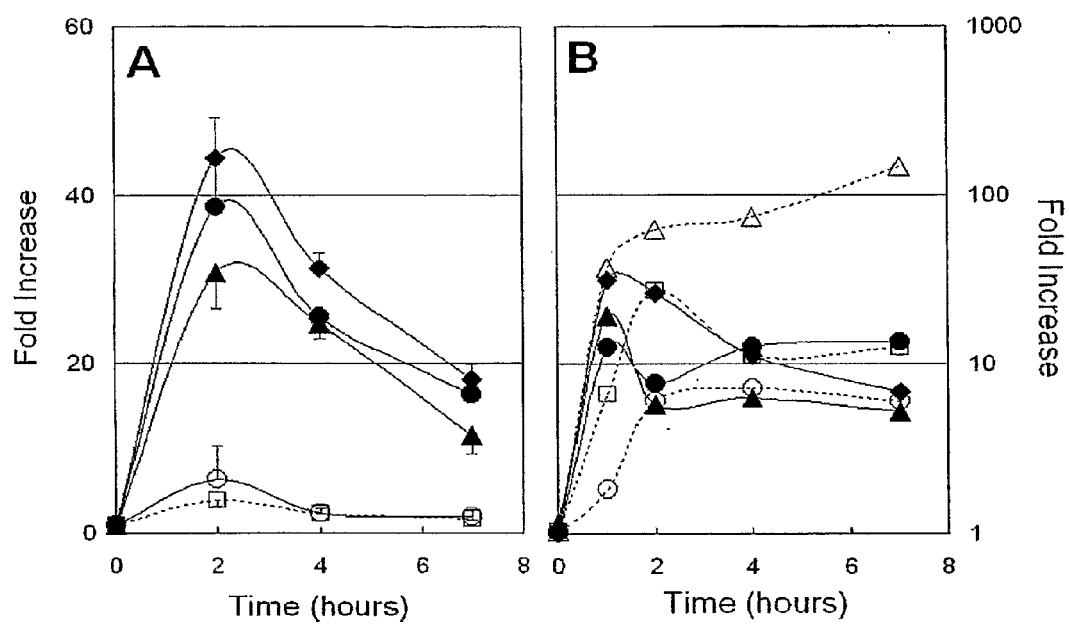
FIGS. 5A-5B show the effect of anti-TCR antibodies on TNFSF and chemokine mRNA expression in peripheral blood leukocytes.

Dose responses and kinetic studies for the anti-TCR stimulation are shown in FIG. 5. FIG. 5 shows the effect of anti-TCR antibody on TNFSF and chemokine mRNA expression in peripheral blood leukocytes. FIG. 5A shows the dose response and kinetics of the stimulus. Triplicate aliquots of 60 μl each of heparinized whole blood were mixed with 10 (●), 1 (♦) or 0.1 (▲) μg/mL mouse anti-human α/β TCR IgG1κ, PBS (o) or 10 (□) μg/ml purified mouse IgG1κ, and incubated at 37° C. for 0-7 hours. Then TNFSF-2 mRNA was quantified as described above. FIG. 5B shows the kinetics of the stimulus. Triplicate aliquots of 60 μL each of heparinized whole blood were mixed with 10 μg/ml mouse anti-human α/β TCR IgG1κ, or 10 μg/ml purified mouse IgG1κ, and incubated at 37° C. for 2 hours. TNFSF-2 (●), TNFSF-5 (□), TNFSF-6 (▲), TNFSF-9 (♦), TNFSF-14 (o), and CXCL-10 (Δ) mRNA were then quantified as described above. The fold increase was calculated by the values of mouse IgG1κ as control. Each data was the mean±standard deviation (A) or mean (B) from triplicate aliquots of whole blood.

In addition to the anti-TCR and HAG described above, other stimulating agents, such as phorbol myristate acetate (PMA), phytohemagglutinin (PHA), wheat germ agglutinin (WGA), concanavalin-A (Con-A), lipopolysaccharides (LPS), jacalin, fucoidan, heat-aggregated IgA, heat-aggregated IgE, and heat-aggregated IgM, also induce different subtypes of TNFSF and chemokines in whole blood taken from healthy individuals, as shown in FIGS. 6-12 and 14-16. The protocol followed in these assays was the same as that given above, with the exception of the different stimulus employed in each case. In FIGS. 6-16, data are expressed in terms of the cycle threshold (Ct), which is the number of cycles of PCR required to generate certain amounts of PCR products. The ΔCt values were obtained by subtracting Ct values of un-stimulated samples from stimulated samples. Since Ct is a log scale, 1 ΔCt unit indicates a change in quantity by a factor of 2. Because a higher expression level reduces the number of PCR cycles required to generate a standard amount of products, a negative ΔCt value indicates an increase in expression.

Figure 6:
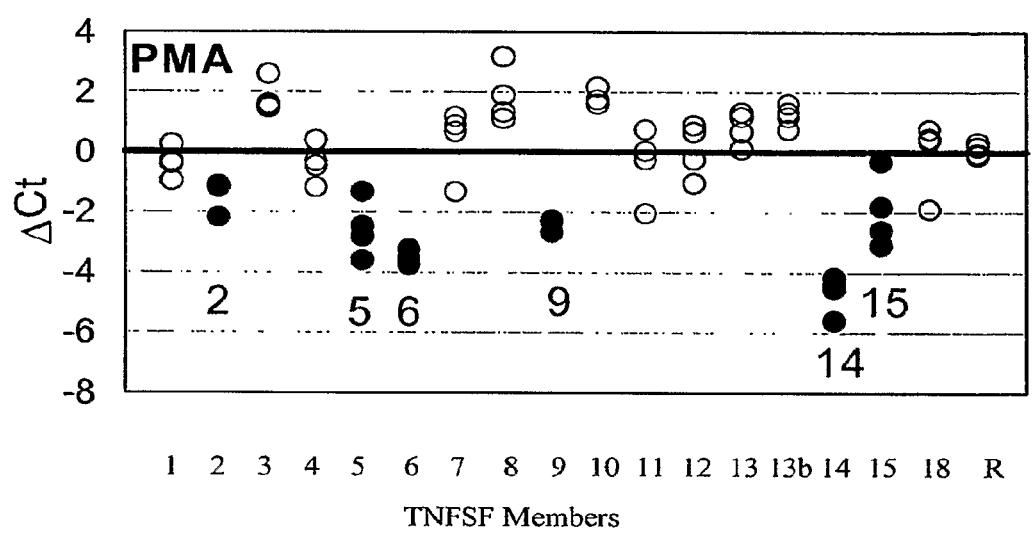
FIG. 6 shows the results of stimulation of whole blood of healthy individuals with phorbol myristate acetate (PMA).
Figure 7:
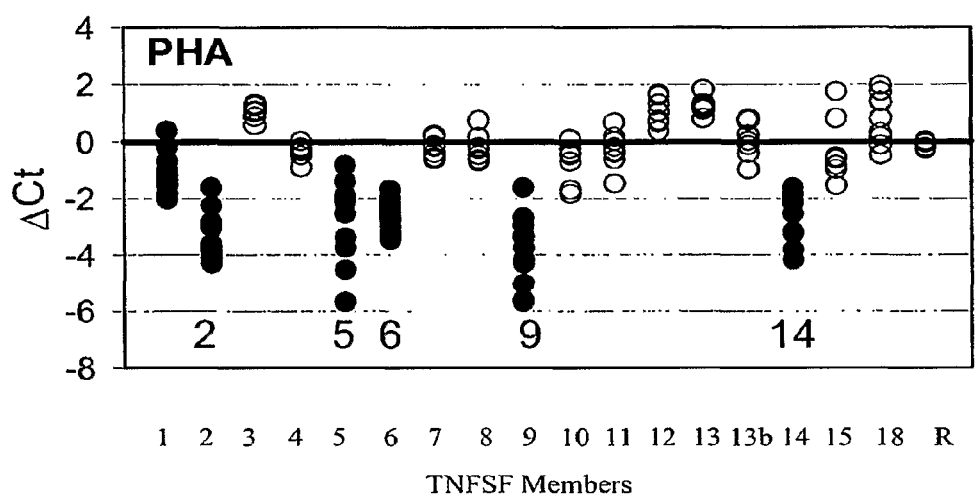
FIG. 7 shows the results of stimulation of whole blood of healthy individuals with phytohemagglutinin (PHA).
Figure 8:
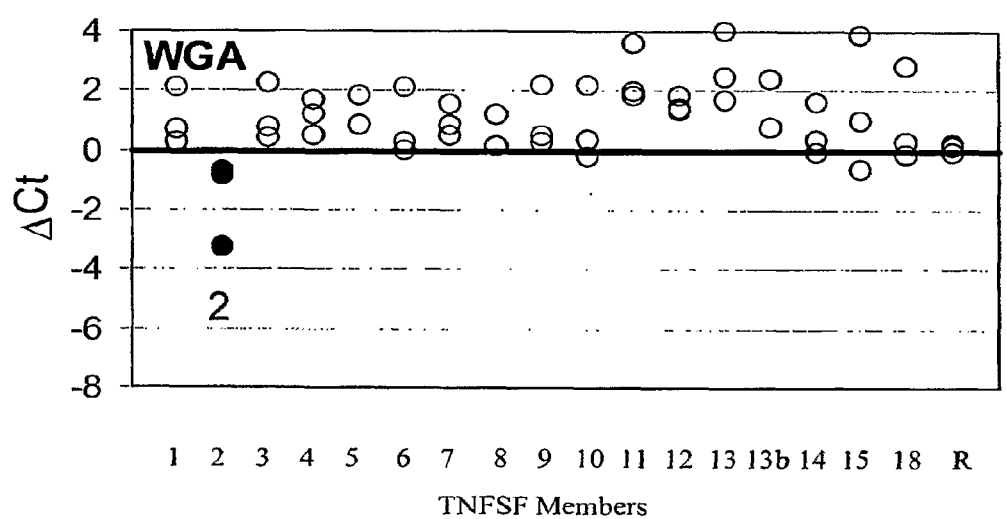
FIG. 8 shows the results of stimulation of whole blood of healthy individuals with wheat germ agglutinin (WGA)
Figure 9:
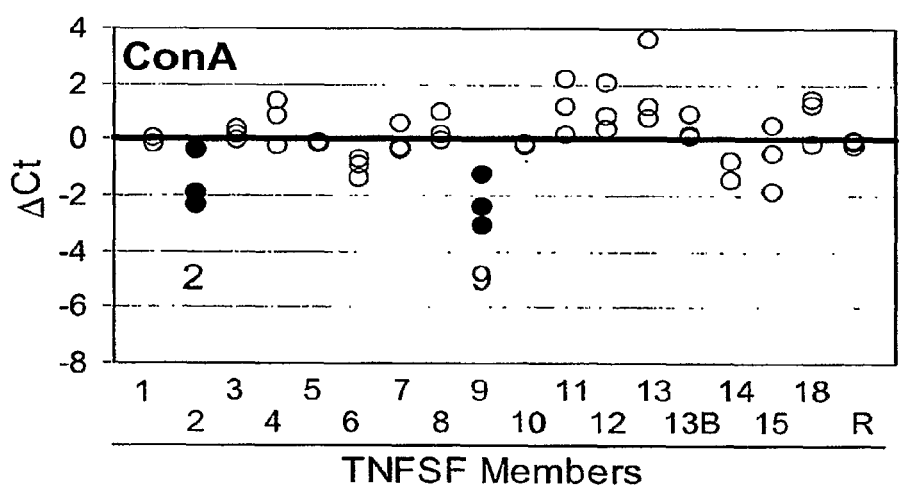
FIG. 9 shows the results of stimulation of whole blood of healthy individuals with concanavalin-A (ConA).
Figure 10:
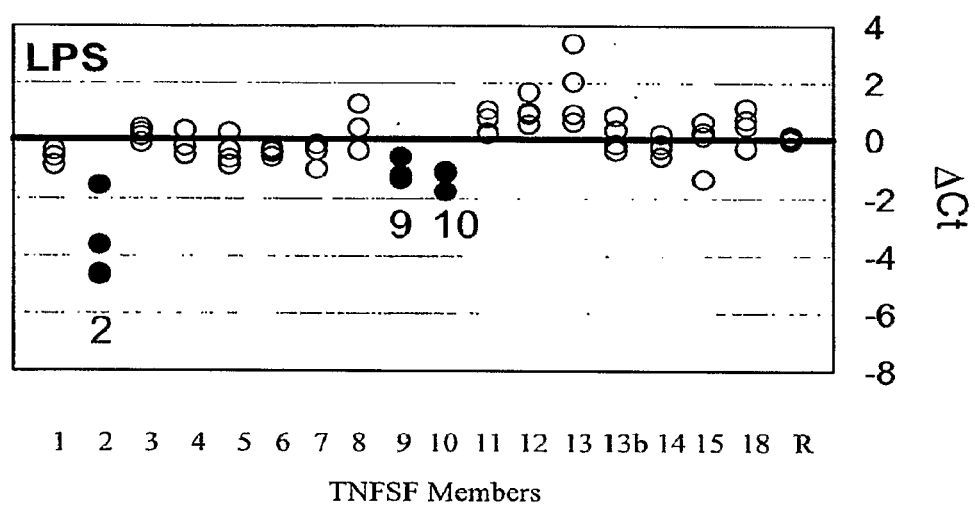
FIG. 10 shows the results of stimulation of whole blood of healthy individuals with lipopolysaccharides (LPS).
Figure 11:
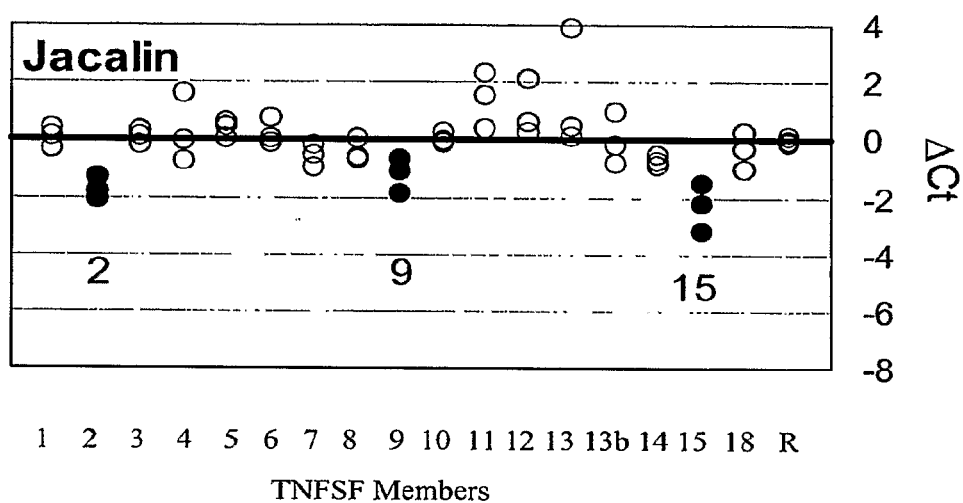
FIG. 11 shows the results of stimulation of whole blood of healthy individuals with jacalin.
Figure 12:
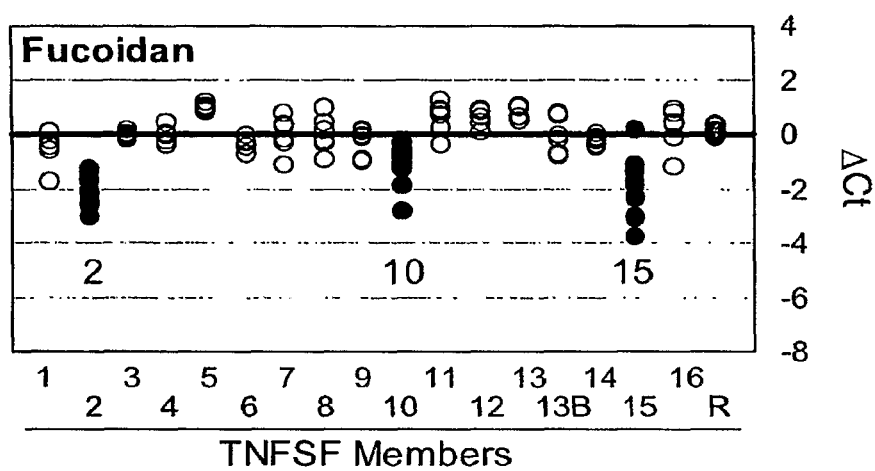
FIG. 12 shows the results of stimulation of whole blood of healthy individuals with fucoidan.
Figure 13A:
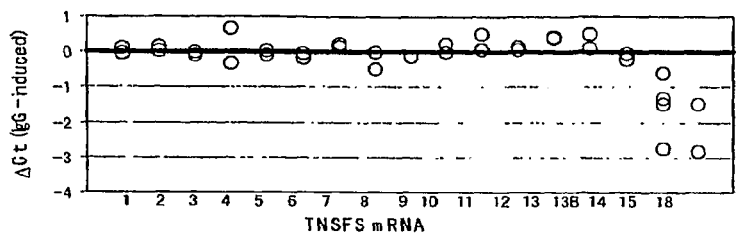
Figure 13B:
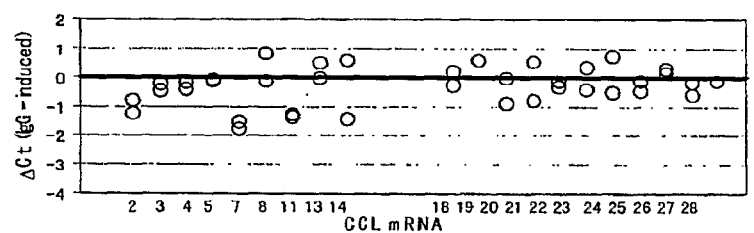
Figure 13C:
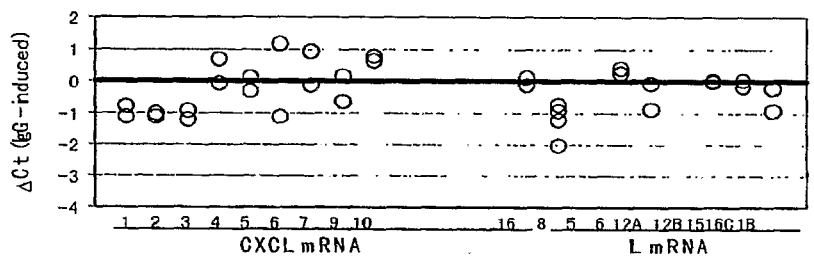
Figure 13D:
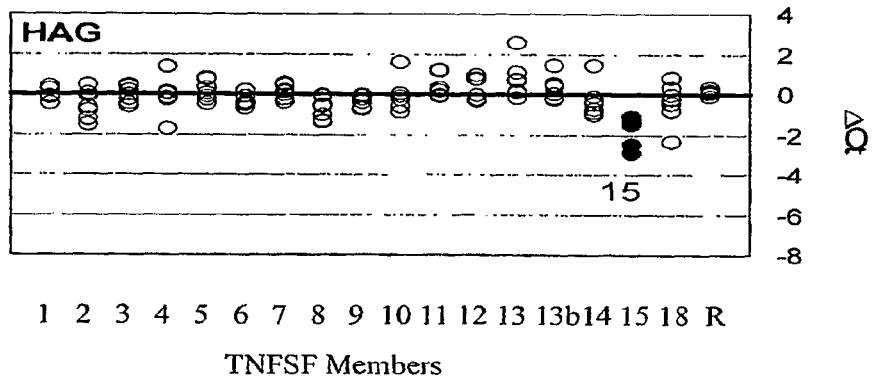
Figure 14A:
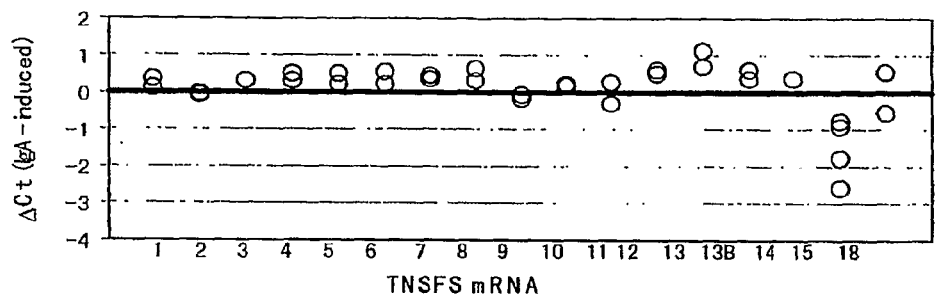
FIGS. 14A-14C show the results of stimulation of whole blood of healthy individuals with heat-aggregated IgA.
Figure 14B:
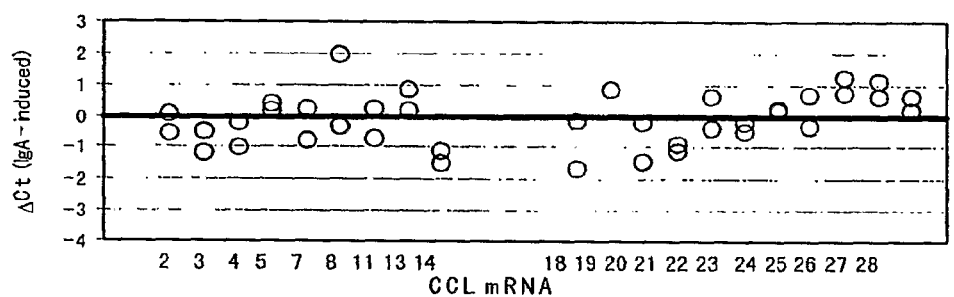
Figure 14C:
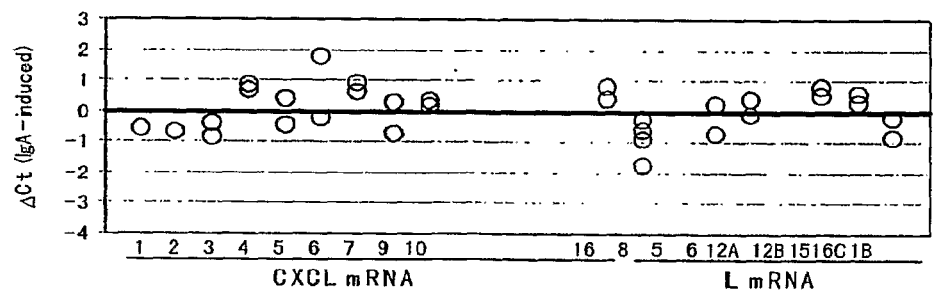
Figure 15A:
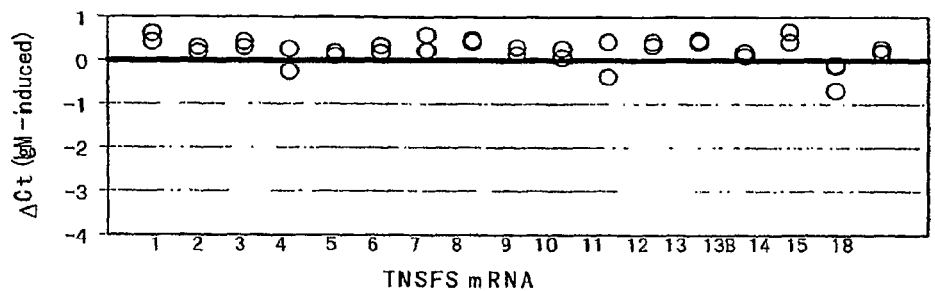
FIGS. 15A-15C show the results of stimulation of whole blood of healthy individuals with heat-aggregated IgM.
Figure 15B:
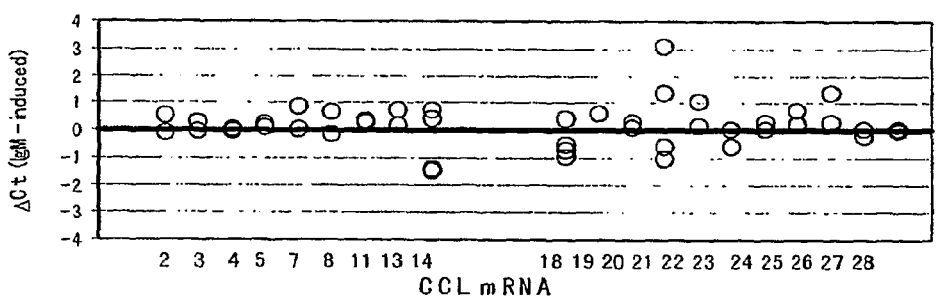
Figure 15C:
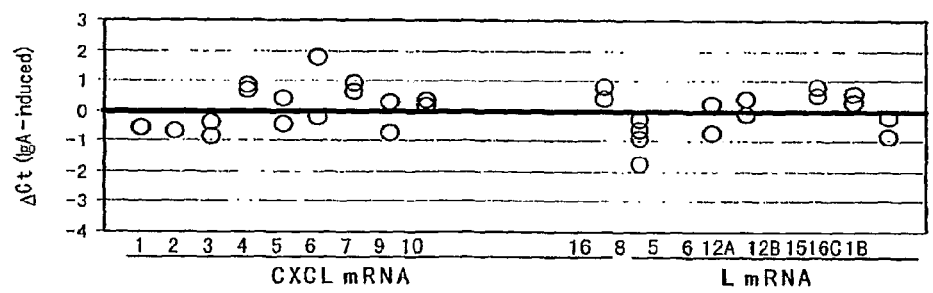
Figure 16A:
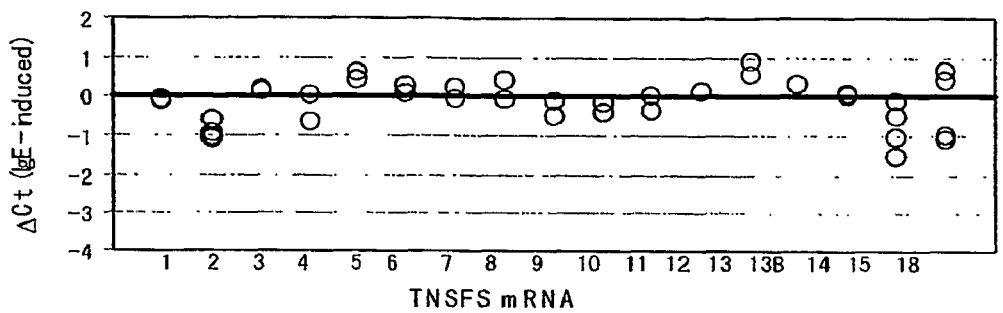
FIGS. 16A-16C show the results of stimulation of whole blood of healthy individuals with heat-aggregated IgE.
Figure 16B:
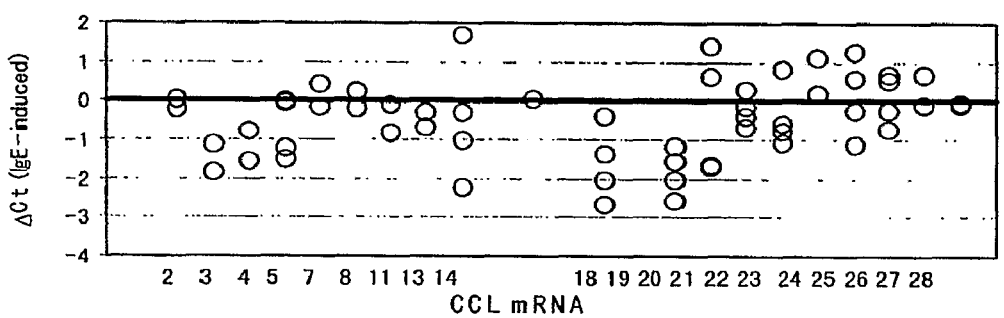
Figure 16C:
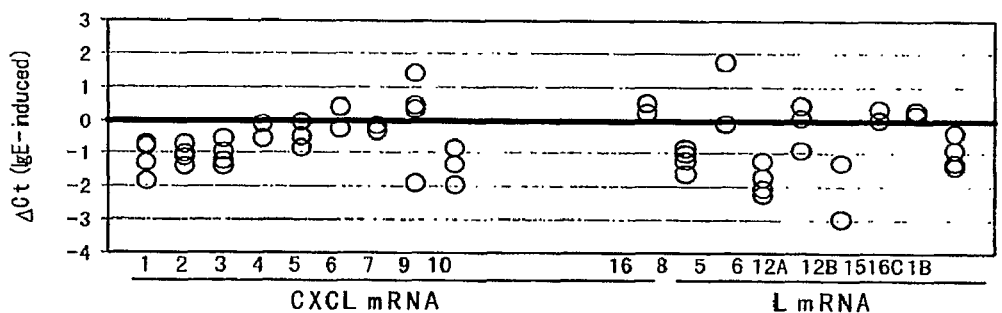

Many of these agents exhibit a stimulus pattern similar to that of anti-TCR. In particular, PMA and PHA stimulate the same TNFSF subtypes as does anti-TCR in CD patients (TNFSF-2, -5, -6, and -14), as shown in FIGS. 6 and 7. Furthermore, WGA, ConA, LPS, jacalin, and fucoidan all stimulate the TNFSF-2 subtype that is known to be linked to CD, as shown in FIGS. 8-12. As shown in FIG. 16, heat-aggregated IgE stimulates TNFSF-2, as well as CCL-3 and -4 and CXCL-10. Finally, heat-aggregated IgA stimulates CCL-2, -3, and -4, as shown in FIG. 14. Because of the similarity of the stimulus patterns to the anti-TCR pattern described above, these agents will also be useful in assessing the therapeutic options for CD patients and in screening for new drugs for treating CD.

Cytotoxic assays have generally been used to study actual cell death resulting from the activity of the immune system, such as that which is believed to occur in CD. Cytotoxic assays are generally conducted by incubating $^{51}$Cr-loaded target cells with effector cells at various ratios, and quantifying the amounts of $^{51}$Cr radioactivity released from the dead or damaged cells (see Dunkley et al., J Immunol Methods 6, 39 (1974)). Radioactive materials have been replaced with non-radioactive materials, such as fluorometric materials, in some cases (see Kruger-Krasagakes et al., J Immunol Methods 156, 1 (1992)), but the basic principle is unchanged. The results of cytotoxic assays are thus reflective of actual cell death.

However, cytotoxic assays are performed under non-physiological experimental conditions, and complex cell-to-cell and cell-to-plasma interactions are difficult to assess in the course of such studies. Furthermore, cytotoxic assays do not indicate which TNFSF member is responsible for cell death. Once effector cells recognize the target cells, the effector cells' function is not only to kill the target, but also recruit other effector cells, because a single effector cell is not enough to kill many target cells. This recruitment function is thought to be represented by the release of chemotactic factors. The identity of such chemotactic factors released by effector cells would not be revealed by classic cytotoxic assays. The assay system set forth in this disclosure is, however, capable of identifying many classes of gene expression in effector cells simultaneously.

Identification of responsible TNFSF and chemokine subtypes is critically important, because these molecules react with specific receptors on the target cells or leukocytes. For example, according to UniGene's Expression Sequence Tag (EST) profile database, the receptor for TNFSF-2 (Tumor Necrosis Factor Receptor Super Family (TNFRSF)-1A) is present in the small intestine, but receptors for TNFSF-5, 6, and 14 (TNFRSF-5, 6, and 14) are not. Thus, enhanced TNFSF-2 activity in CD patients (FIG. 1B, FIG. 3A) may be linked to damage to the small intestine, which is a major CD disease site. Furthermore, the receptor of CCL-2 (CCR-2) is known as the receptor of monocyte chemoattractant protein-1, and the receptor for CXCL-10 (CXCR-3) is responsible for the migration of NK cells and T cells (UniGene database). As noted above, the disclosed data indicate that the effector leukocytes of CD patients transcribe an increased amount of CCL-2 and CXCL-10 mRNA when stimulated, which may explain the various leukocyte infiltrations seen at CD disease sites.

The use of whole blood is preferable to using isolated leukocytes in culture media, because the former is more physiological than the latter, and whole populations of leukocytes can be screened. Longer incubation of whole blood may produce additional artifacts. Thus, the ideal way is to identify early signals of killer and recruitment signals in whole blood during a short period of incubation by switching in vitro to ex vivo. The transcription of mRNA is an earlier event than either protein synthesis or the final biological outcomes Thus, mRNA is a logical target of this study.

Among many TNFSF, CCL, CXCL, and interleukin mRNAs, the data in this disclosure show that FcR and TCR induce different subclasses of genes, as shown in FIG. 1.

Recent studies have suggested that TNFSF-2 is one of the major factors in CD (see Isaacs et al., Inflamm. Bowel Dis. 11 Suppl 1, S3 (2005)). In fact, Remicade®, which is a monoclonal antibody against TNF-α, is used clinically for patients with severe CD and a poor history with other conventional treatments, as noted above. Although TNF-α plays a crucial role in the pathogenesis of CD in lesions, the data set forth in the present disclosure indicate an underlying hyperfunction of TCR inducibility of several TNFSF members, including TNF-α (TNFSF-2) in circulating leukocytes in peripheral blood, which has not previously been observed. Since the present method uses whole blood, not intestinal tissues, it may be used as a diagnostic test for CD to evaluate possible responsiveness to TNF-α therapy, and to monitor the therapeutic response.

Specifically, in a preferred embodiment of a method for determining whether a human having CD is likely to respond to a therapy targeting TNF-α activity, such as therapy employing an anti-TNF-α monoclonal antibody, whole blood is obtained from a CD patient and samples of the blood are subjected to anti-TCR antibody stimulation and optionally to control stimulation (10 mg/ml purified mouse IgG1κ), as described above. The mRNA level of TNFSF-2 may be measured in the samples as described above. A CD patient having a significantly elevated level of TNFSF-2 mRNA after stimulation with anti-TCR antibody (as indicated, for example, by a fold change of greater than 1.7) is a good candidate for therapy targeting TNF-α.

Alternatively, the level of one or more other mRNAs that are differentially transcribed in response to a T-cell stimulus, such as TNFSF-5, TNFSF-6, TNFSF-14, CCL-2, CCL-3, CCL-4, or CXCL-10 may be measured. A CD patient having a significantly elevated (such as a 1.7-fold or greater change) post-stimulation level of one or more of these mRNAs may be a good candidate for a therapy that targets proteins associated with these mRNAs.

Furthermore, in a preferred embodiment of a method of evaluating the effectiveness of CD treatment targeting one or more of TNFSF-2, TNFSF-5, TNFSF-6, TNFSF-14, CCL-2, CCL-3, CCL-4, and CXCL-10 TNF-α in a patient, a first ratio of the amount of the mRNA in whole blood after T-cell stimulation using anti-TCR antibody or another stimulus in vitro to the amount after control stimulation in vitro is obtained prior to the initiation of the treatment. The course of treatment is then begun. At some point during or after the treatment, a second ratio of the amount of the mRNA in whole blood after anti-TCR antibody stimulation in vitro to the amount after control stimulation in vitro is obtained. A significant difference in the ratios can indicate the effectiveness of the therapy. For example, where the treatment is the administration of infliximab, the measured mRNA is TNFSF-2, and the second ratio is larger than the first ratio, this can indicate the effectiveness of the therapy. The reason that an increase in inducibility with respect to an mRNA associated with TNF-α can indicate successful inactivation is that when secreted TNF-α is successfully inactivated by a therapeutic agent such as Remicade®, a feedback mechanism operates in the T-cells by which more TNFSF-2 mRNA is transcribed.

In other cases, a smaller second ratio with respect to a CD-associated mRNA may indicate a successful therapy. Such a result indicates that the T cells have become less inducible with respect to the measured mRNA after treatment. For example, therapy that reduced the inducibility of the leukocytes with respect to TNFSF-2, and thus the amount of TNF-α released, would presumably be of benefit in ameliorating the symptoms of CD. Similarly, reductions in the amount of CCL-2 and CXCL-10 transcribed would likely lead to reduced leukocyte infiltration and less severe symptoms.

Importantly, this ex vivo method can also be used for the screening of compounds which inhibit anti-TCR-mediated TNFα mRNA expression. Such compounds will be interesting drug targets, because a monoclonal antibody against TNF-α reacts with already-released TNF-α at the lesion, whereas these new drug candidates will block TNF-α production of leukocytes at the transcription level. This is a new strategy for drug development against autoimmune disease.

In an embodiment of a method of screening drug compounds using the disclosed system and thereby identifying a putative agent for treating CD, whole blood is obtained from CD patients that are responders, in that their leukocytes exhibit at least a 1.7-fold increase in the level of a CD-associated mRNA when exposed to a t-cell stimulation such as anti-TCR. A first ratio of the amount of the mRNA in whole blood after T-cell stimulus using anti-TCR antibody or another stimulus in vitro to the amount after control stimulation in vitro is calculated. Further whole blood samples from the subjects are exposed in vitro to the drug compound, and then differentially stimulated as described above. A second ratio of the amount of the mRNA in whole blood after the T-cell stimulus in vitro to the amount after control stimulation in vitro is then calculated. A significant difference in the ratios can indicate that the drug compound is a candidate for further investigation as a potential therapeutic for CD.

Additionally, in a preferred embodiment of a method of monitoring the state of the disease in a CD patient by measuring levels of one or more of TNFSF-2, TNFSF-5, TNFSF-6, TNFSF-14, CCL-2, CCL-3, CCL-4, and CXCL-10 mRNAs in samples comprising leukocytes obtained from the patient, a first ratio of the amount of the mRNA in whole blood after T-cell stimulus using anti-TCR antibody or other stimulus in vitro to the amount after control stimulation in vitro is obtained at a first time. At a second time subsequent to the first time, a second ratio of the amount of the mRNA in whole blood after the T-cell stimulus in vitro to the amount after control stimulation in vitro is obtained. A significant difference in the ratios can indicate a change in the disease state. For example, when the second ratio is larger than the first, this can indicate disease progression, while a larger first ratio can indicate that the disease has regressed.

The invention claimed is:

1. A method of determining whether a human having Crohn's disease is likely to respond to immunosuppressive therapy, comprising:
   stimulating leukocytes with an anti-T-cell receptor antibody in vitro in a first sample that comprises leukocytes from the human;
   after the stimulation, measuring the amount of an mRNA encoding a tumor necrosis factor superfamily member in the first sample;
   exposing leukocytes in vitro in a second sample comprising leukocytes from the human to a control stimulus;
   measuring the amount of the mRNA in the second sample after exposing; and
   determining a ratio of the amount of the mRNA in the first sample to the amount of the mRNA in the second sample, wherein a ratio of at least about 1.7:1 indicates that the human is likely to respond to said immunosuppressive therapy.

2. The method of claim 1, wherein at least one of the first and second samples comprises whole blood.

3. The method of claim 1, wherein the control stimulus comprises a purified control immunoglobulin.

4. The method of claim 1, wherein the therapy targets TNF-α activity.

5. The method of claim 4, wherein the therapy comprises administration of infliximab.

6. The method of claim 1, wherein the therapy comprises administration of an agent selected from the group consisting of cyclosporine A and tacrolimus.

7. A method of evaluating the state of Crohn's disease in a human, comprising:
   stimulating leukocytes with an anti-T-cell receptor antibody in vitro in a first sample that comprises leukocytes and is obtained at a first time from the human;
   after the stimulation, measuring the amount of an mRNA encoding a tumor necrosis factor superfamily member in the first sample;
   exposing leukocytes in vitro to a control stimulus in a second sample comprising leukocytes obtained from the human at the first time;
   measuring the amount of the mRNA in the second sample after exposing;
   determining a first ratio of the amount of the mRNA in the first sample to the amount of the mRNA in the second sample;
   stimulating leukocytes with an anti-T-cell receptor antibody in vitro in a third sample that comprises leukocytes and is obtained from the human at a second time that is subsequent to the first time;
   after the stimulation, measuring the amount of the mRNA in the third sample;
   exposing leukocytes in vitro to a control stimulus in a fourth sample comprising leukocytes obtained from the human at the second time;
   measuring the amount of the mRNA in the fourth sample after exposing;
   determining a second ratio of the amount of the mRNA in the third sample to the amount of the mRNA in the fourth sample; and
   comparing the first and second ratios, wherein a statistically significant difference in the first and second ratios is indicative of a change in the disease state.

8. The method of claim 7, wherein the control stimulus comprises a purified control immunoglobulin.

9. The method of claim 7, wherein at least one of the first, second, third and fourth samples comprises whole blood.

10. The method of claim 7, wherein the significant difference in the ratios is that the second ratio is greater than the first ratio, and the change in disease state is a progression of the disease.

11. The method of claim 7, wherein the significant difference in the ratios is that the first ratio is greater than the second ratio, and the change in disease state is a regression of the disease.

12. The method of any of claims 1 and 7 wherein the tumor necrosis factor superfamily ("TNFSF") member is selected from the group consisting of TNFSF-2, TNFSF-5, TNFSF-6, and TNFSF-14.

13. The method of claim 12, wherein the TNFSF member is selected from the group consisting of TNFSF-2 and TNFSF-14.

* * * * *

UNITED STATES PATENT AND TRADEMARK OFFICE
CERTIFICATE OF CORRECTION

PATENT NO. : 7,838,239 B2
APPLICATION NO. : 12/296425
DATED : November 23, 2010
INVENTOR(S) : Mitsuhashi et al.

It is certified that error appears in the above-identified patent and that said Letters Patent is hereby corrected as shown below:

On Item 56, page 2, column 1, line 8, under Other Publications, delete "pateints" and insert -- patients --, therefor.

On Item 56, page 2, column 1, line 20, under Other Publications, delete "Chemotherapeuytic" and insert -- Chemotherapeutic --, therefor.

On Item 56, page 2, column 1, line 38, under Other Publications, delete "Internatiol" and insert -- International, --, therefor.

At column 3, line 2, delete "IgG.," and insert -- IgG, --, therefor.

At column 5, line 60, delete "(WGA)" and insert -- (WGA). --, therefor.

At column 6, line 2, after "fucoidan." insert -- FIGS. 13A-13D show the results of stimulation of whole blood of healthy individuals with heat-aggregated IgG. --, on Col. 6, Line 3, as a new paragraph, therefor.

At column 11, line 49, delete "2-mercaptethanol" and insert -- 2-mercaptoethanol --, therefor.

At column 15, line 67, delete "outcomes" and insert -- outcomes. --, therefor.

Signed and Sealed this
Fourth Day of October, 2011

David J. Kappos
*Director of the United States Patent and Trademark Office*

SEQUENCE LISTING

```
<160> NUMBER OF SEQ ID NOS: 110

<210> SEQ ID NO 1
<211> LENGTH: 22
<212> TYPE: DNA
<213> ORGANISM: Artificial Sequence
<220> FEATURE:
<223> OTHER INFORMATION: PCR Primer

<400> SEQUENCE: 1
cagctatcca cccacacaga tg                                              22

<210> SEQ ID NO 2
<211> LENGTH: 22
<212> TYPE: DNA
<213> ORGANISM: Artificial Sequence
<220> FEATURE:
<223> OTHER INFORMATION: PCR Primer

<400> SEQUENCE: 2
cgaaggctcc aaagaagaca gt                                              22

<210> SEQ ID NO 3
<211> LENGTH: 20
<212> TYPE: DNA
<213> ORGANISM: Artificial Sequence
<220> FEATURE:
<223> OTHER INFORMATION: PCR Primer

<400> SEQUENCE: 3
tcaatcggcc cgactatctc                                                 20

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
```

-continued cagggcaatg atcccaaagt                                               20

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
agggtgtacg tcaacatcag tca                                           23

<210> SEQ ID NO 6
<211> LENGTH: 18
<212> TYPE: DNA
<213> ORGANISM: Artificial Sequence
<220> FEATURE:
<223> OTHER INFORMATION: PCR Primer

<400> SEQUENCE: 6
cacggcccca aagaaggt                                                 18

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7 gccctcttc caactgaaga a                                              21

<210> SEQ ID NO 8
<211> LENGTH: 25
<212> TYPE: DNA
<213> ORGANISM: Artificial Sequence
<220> FEATURE:
<223> OTHER INFORMATION: PCR Primer

<400> SEQUENCE: 8
ggtattgtca gtggtcacat tcaag                                         25

<210> SEQ ID NO 9
<211> LENGTH: 19
<212> TYPE: DNA
<213> ORGANISM: Artificial Sequence
<220> FEATURE:
<223> OTHER INFORMATION: PCR Primer

<400> SEQUENCE: 9
ccacagttcc gccaaacct                                                19

<210> SEQ ID NO 10
<211> LENGTH: 24
<212> TYPE: DNA
<213> ORGANISM: Artificial Sequence
<220> FEATURE:
<223> OTHER INFORMATION: PCR Primer

<400> SEQUENCE: 10
cacctggttg caattcaaat actc                                          24

<210> SEQ ID NO 11
<211> LENGTH: 24
<212> TYPE: DNA

<213> ORGANISM: Artificial Sequence
<220> FEATURE:
<223> OTHER INFORMATION: PCR Primer

<400> SEQUENCE: 11
tggcagcatc ttcacttcta aatg                                              24

<210> SEQ ID NO 12
<211> LENGTH: 24
<212> TYPE: DNA
<213> ORGANISM: Artificial Sequence
<220> FEATURE:
<223> OTHER INFORMATION: PCR Primer

<400> SEQUENCE: 12
gaaatgagtc cccaaaacat ctct                                              24

<210> SEQ ID NO 13
<211> LENGTH: 22
<212> TYPE: DNA
<213> ORGANISM: Artificial Sequence
<220> FEATURE:
<223> OTHER INFORMATION: PCR Primer

<400> SEQUENCE: 13
cacactctgc accaacctca ct                                                22

<210> SEQ ID NO 14
<211> LENGTH: 23
<212> TYPE: DNA
<213> ORGANISM: Artificial Sequence
<220> FEATURE:
<223> OTHER INFORMATION: PCR Primer

<400> SEQUENCE: 14
tgcactccaa agaaggtctc atc                                               23

<210> SEQ ID NO 15
<211> LENGTH: 24
<212> TYPE: DNA
<213> ORGANISM: Artificial Sequence
<220> FEATURE:
<223> OTHER INFORMATION: PCR Primer

<400> SEQUENCE: 15
accaccatat cagtcaatgt ggat                                              24

<210> SEQ ID NO 16
<211> LENGTH: 25
<212> TYPE: DNA
<213> ORGANISM: Artificial Sequence
<220> FEATURE:
<223> OTHER INFORMATION: PCR Primer

<400> SEQUENCE: 16
gaagatggac aacacattct caaga                                             25

<210> SEQ ID NO 17
<211> LENGTH: 23
<212> TYPE: DNA
<213> ORGANISM: Artificial Sequence
<220> FEATURE:
<223> OTHER INFORMATION: PCR Primer

<400> SEQUENCE: 17
agctacaaag aggacacgaa gga                                               23

<210> SEQ ID NO 18
<211> LENGTH: 24
<212> TYPE: DNA
<213> ORGANISM: -Artificial Sequence
<220> FEATURE:
<223> OTHER INFORMATION: PCR Primer

<400> SEQUENCE: 18
cgcagctcta gttgaaagaa gaca                                          24

<210> SEQ ID NO 19
<211> LENGTH: 26
<212> TYPE: DNA
<213> ORGANISM: Artificial Sequence
<220> FEATURE:
<223> OTHER INFORMATION: PCR Primer

<400> SEQUENCE: 19
gggaatattt gagcttaagg aaaatg                                        26

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
aaaaggcccc gaaaaaactg                                               20

<210> SEQ ID NO 21
<211> LENGTH: 30
<212> TYPE: DNA
<213> ORGANISM: Artificial Sequence
<220> FEATURE:
<223> OTHER INFORMATION: PCR Primer

<400> SEQUENCE: 21
gagtatcttc aactaatggt gtacgtcact                                    30

<210> SEQ ID NO 22
<211> LENGTH: 21
<212> TYPE: DNA
<213> ORGANISM: Artificial Sequence
<220> FEATURE:
<223> OTHER INFORMATION: PCR Primer

<400> SEQUENCE: 22
tggtgcttcc tcctttcatc a                                             21

<210> SEQ ID NO 23
<211> LENGTH: 24
<212> TYPE: DNA
<213> ORGANISM: Artificial Sequence
<220> FEATURE:
<223> OTHER INFORMATION: PCR Primer

<400> SEQUENCE: 23
tactgtcagg tgcactttga tgag                                          24

<210> SEQ ID NO 24
<211> LENGTH: 19
<212> TYPE: DNA
<213> ORGANISM: Artificial Sequence
<220> FEATURE:

```
<223> OTHER INFORMATION: PCR Primer

<400> SEQUENCE: 24
gcagtggctg agaattcct                                                    19

<210> SEQ ID NO 25
<211> LENGTH: 22
<212> TYPE: DNA
<213> ORGANISM: Artificial Sequence
<220> FEATURE:
<223> OTHER INFORMATION: PCR Primer

<400> SEQUENCE: 25
atatggtgtc cgaatccagg at                                                22

<210> SEQ ID NO 26
<211> LENGTH: 21
<212> TYPE: DNA
<213> ORGANISM: Artificial Sequence
<220> FEATURE:
<223> OTHER INFORMATION: PCR Primer

<400> SEQUENCE: 26
cctgacccat ggtgaaagtc a                                                 21

<210> SEQ ID NO 27
<211> LENGTH: 25
<212> TYPE: DNA
<213> ORGANISM: Artificial Sequence
<220> FEATURE:
<223> OTHER INFORMATION: PCR Primer

<400> SEQUENCE: 27
atgcctgaaa cactacccaa taatt                                             25

<210> SEQ ID NO 28
<211> LENGTH: 24
<212> TYPE: DNA
<213> ORGANISM: Artificial Sequence
<220> FEATURE:
<223> OTHER INFORMATION: PCR Primer

<400> SEQUENCE: 28
gcaagttgga gttcatctcc ttct                                              24

<210> SEQ ID NO 29
<211> LENGTH: 18
<212> TYPE: DNA
<213> ORGANISM: Artificial Sequence
<220> FEATURE:
<223> OTHER INFORMATION: PCR Primer

<400> SEQUENCE: 29
cgtccgtgtg ctggatga                                                     18

<210> SEQ ID NO 30
<211> LENGTH: 22
<212> TYPE: DNA
<213> ORGANISM: Artificial Sequence
<220> FEATURE:
<223> OTHER INFORMATION: PCR Primer

<400> SEQUENCE: 30
catgaaagcc ccgaagtaag ac                                                22
```

<210> SEQ ID NO 31
<211> LENGTH: 23
<212> TYPE: DNA
<213> ORGANISM: Artificial Sequence
<220> FEATURE:
<223> OTHER INFORMATION: PCR Primer

<400> SEQUENCE: 31
tgcgaagtag gtagcaactg gtt                                             23

<210> SEQ ID NO 32
<211> LENGTH: 22
<212> TYPE: DNA
<213> ORGANISM: Artificial Sequence
<220> FEATURE:
<223> OTHER INFORMATION: PCR Primer

<400> SEQUENCE: 32
ccattagctt gtccccttct tg                                              22

<210> SEQ ID NO 33
<211> LENGTH: 26
<212> TYPE: DNA
<213> ORGANISM: Artificial Sequence
<220> FEATURE:
<223> OTHER INFORMATION: PCR Primer

<400> SEQUENCE: 33
cggctgtata aaacaaaga catgat                                           26

<210> SEQ ID NO 34
<211> LENGTH: 22
<212> TYPE: DNA
<213> ORGANISM: Artificial Sequence
<220> FEATURE:
<223> OTHER INFORMATION: PCR Primer

<400> SEQUENCE: 34
tccccaacat gcaattcata ag                                              22

<210> SEQ ID NO 35
<211> LENGTH: 24
<212> TYPE: DNA
<213> ORGANISM: Artificial Sequence
<220> FEATURE:
<223> OTHER INFORMATION: PCR Primer

<400> SEQUENCE: 35
gaagatggaa aagcgatttg tctt                                            24

<210> SEQ ID NO 36
<211> LENGTH: 21
<212> TYPE: DNA
<213> ORGANISM: Artificial Sequence
<220> FEATURE:
<223> OTHER INFORMATION: PCR Primer

<400> SEQUENCE: 36
gggcatgttt tctgcttgag a                                               21

<210> SEQ ID NO 37
<211> LENGTH: 20
<212> TYPE: DNA
<213> ORGANISM: Artificial Sequence
<220> FEATURE:
<223> OTHER INFORMATION: PCR Primer

```
<400> SEQUENCE: 37
gctcttggag ctgcctacgt                                            20

<210> SEQ ID NO 38
<211> LENGTH: 24
<212> TYPE: DNA
<213> ORGANISM: Artificial Sequence
<220> FEATURE:
<223> OTHER INFORMATION: PCR Primer

<400> SEQUENCE: 38
aaggtctctt tcaccaatgc actt                                       24

<210> SEQ ID NO 39
<211> LENGTH: 24
<212> TYPE: DNA
<213> ORGANISM: Artificial Sequence
<220> FEATURE:
<223> OTHER INFORMATION: PCR Primer

<400> SEQUENCE: 39
tcatcactgg tcttttggag tttg                                       24

<210> SEQ ID NO 40
<211> LENGTH: 20
<212> TYPE: DNA
<213> ORGANISM: Artificial Sequence
<220> FEATURE:
<223> OTHER INFORMATION: PCR Primer

<400> SEQUENCE: 40
tctgcacagc tctggcttgt                                            20

<210> SEQ ID NO 41
<211> LENGTH: 27
<212> TYPE: DNA
<213> ORGANISM: Artificial Sequence
<220> FEATURE:
<223> OTHER INFORMATION: PCR Primer

<400> SEQUENCE: 41
tgctaaagaa cttagatgtc agtgcat                                    27

<210> SEQ ID NO 42
<211> LENGTH: 23
<212> TYPE: DNA
<213> ORGANISM: Artificial Sequence
<220> FEATURE:
<223> OTHER INFORMATION: PCR Primer

<400> SEQUENCE: 42
tggtccactc tcaatcactc tca                                        23

<210> SEQ ID NO 43
<211> LENGTH: 20
<212> TYPE: DNA
<213> ORGANISM: Artificial Sequence
<220> FEATURE:
<223> OTHER INFORMATION: PCR Primer

<400> SEQUENCE: 43
gcaggccctg aatttcaaca                                            20

<210> SEQ ID NO 44
<211> LENGTH: 29
```

```
<212> TYPE: DNA
<213> ORGANISM: Artificial Sequence
<220> FEATURE:
<223> OTHER INFORMATION: PCR Primer

<400> SEQUENCE: 44
gaagtatgca gagcttgatt ttagttttta                              29

<210> SEQ ID NO 45
<211> LENGTH: 29
<212> TYPE: DNA
<213> ORGANISM: Artificial Sequence
<220> FEATURE:
<223> OTHER INFORMATION: PCR Primer

<400> SEQUENCE: 45
gaagtatgca gagcttgatt ttagttttta                              29

<210> SEQ ID NO 46
<211> LENGTH: 20
<212> TYPE: DNA
<213> ORGANISM: Artificial Sequence
<220> FEATURE:
<223> OTHER INFORMATION: PCR Primer

<400> SEQUENCE: 46
cccattcgct ccaagatgag                                         20

<210> SEQ ID NO 47
<211> LENGTH: 25
<212> TYPE: DNA
<213> ORGANISM: Artificial Sequence
<220> FEATURE:
<223> OTHER INFORMATION: PCR Primer

<400> SEQUENCE: 47
tgaagtgctt tctcttggag ttaca                                   25

<210> SEQ ID NO 48
<211> LENGTH: 26
<212> TYPE: DNA
<213> ORGANISM: Artificial Sequence
<220> FEATURE:
<223> OTHER INFORMATION: PCR Primer

<400> SEQUENCE: 48
cattcccatt agaagacaaa ctgttg                                  26

<210> SEQ ID NO 49
<211> LENGTH: 22
<212> TYPE: DNA
<213> ORGANISM: Artificial Sequence
<220> FEATURE:
<223> OTHER INFORMATION: PCR Primer

<400> SEQUENCE: 49
aaaacctctt gggaagcatg ag                                      22

<210> SEQ ID NO 50
<211> LENGTH: 20
<212> TYPE: DNA
<213> ORGANISM: Artificial Sequence
<220> FEATURE:
<223> OTHER INFORMATION: PCR Primer

<400> SEQUENCE: 50
```
gggaccccga ggacagtact                                               20

<210> SEQ ID NO 51
<211> LENGTH: 20
<212> TYPE: DNA
<213> ORGANISM: Artificial Sequence
<220> FEATURE:
<223> OTHER INFORMATION: PCR Primer

<400> SEQUENCE: 51
ccattgtggc caaggagatc                                               20

<210> SEQ ID NO 52
<211> LENGTH: 19
<212> TYPE: DNA
<213> ORGANISM: Artificial Sequence
<220> FEATURE:
<223> OTHER INFORMATION: PCR Primer

<400> SEQUENCE: 52
tgtccaggtg gtccatgga                                                19

<210> SEQ ID NO 53
<211> LENGTH: 28
<212> TYPE: DNA
<213> ORGANISM: Artificial Sequence
<220> FEATURE:
<223> OTHER INFORMATION: PCR Primer

<400> SEQUENCE: 53
cacagaattt catagctgac tactttga                                      28

<210> SEQ ID NO 54
<211> LENGTH: 22
<212> TYPE: DNA
<213> ORGANISM: Artificial Sequence
<220> FEATURE:
<223> OTHER INFORMATION: PCR Primer

<400> SEQUENCE: 54
tcgcttggtt aggaagatga ca                                            22

<210> SEQ ID NO 55
<211> LENGTH: 23
<212> TYPE: DNA
<213> ORGANISM: Artificial Sequence
<220> FEATURE:
<223> OTHER INFORMATION: PCR Primer

<400> SEQUENCE: 55
ggtattccaa accaaaagaa gca                                           23

<210> SEQ ID NO 56
<211> LENGTH: 26
<212> TYPE: DNA
<213> ORGANISM: Artificial Sequence
<220> FEATURE:
<223> OTHER INFORMATION: PCR Primer

<400> SEQUENCE: 56
gttcagttcc aggtcataca cgtact                                        26

<210> SEQ ID NO 57
<211> LENGTH: 21
<212> TYPE: DNA
<213> ORGANISM: Artificial Sequence

```
<220> FEATURE:
<223> OTHER INFORMATION: PCR Primer

<400> SEQUENCE: 57
agtcgtcttt gtcacccgaa a                                             21

<210> SEQ ID NO 58
<211> LENGTH: 26
<212> TYPE: DNA
<213> ORGANISM: Artificial Sequence
<220> FEATURE:
<223> OTHER INFORMATION: PCR Primer

<400> SEQUENCE: 58
agctcatctc caaagagttg atgtac                                        26

<210> SEQ ID NO 59
<211> LENGTH: 19
<212> TYPE: DNA
<213> ORGANISM: Artificial Sequence
<220> FEATURE:
<223> OTHER INFORMATION: PCR Primer

<400> SEQUENCE: 59
tgtgctgacc ccacacaga                                                19

<210> SEQ ID NO 60
<211> LENGTH: 23
<212> TYPE: DNA
<213> ORGANISM: Artificial Sequence
<220> FEATURE:
<223> OTHER INFORMATION: PCR Primer

<400> SEQUENCE: 60
gctttggagt ttgggttttc ttg                                           23

<210> SEQ ID NO 61
<211> LENGTH: 26
<212> TYPE: DNA
<213> ORGANISM: Artificial Sequence
<220> FEATURE:
<223> OTHER INFORMATION: PCR Primer

<400> SEQUENCE: 61
agagctacac aagaatcacc aacatc                                        26

<210> SEQ ID NO 62
<211> LENGTH: 19
<212> TYPE: DNA
<213> ORGANISM: Artificial Sequence
<220> FEATURE:
<223> OTHER INFORMATION: PCR Primer

<400> SEQUENCE: 62
agacctcctt gccccgttt                                                19

<210> SEQ ID NO 63
<211> LENGTH: 22
<212> TYPE: DNA
<213> ORGANISM: Artificial Sequence
<220> FEATURE:
<223> OTHER INFORMATION: PCR Primer

<400> SEQUENCE: 63
cccagaaagc tgtgatcttc aa                                            22
```

<210> SEQ ID NO 64
<211> LENGTH: 21
<212> TYPE: DNA
<213> ORGANISM: Artificial Sequence
<220> FEATURE:
<223> OTHER INFORMATION: PCR Primer

<400> SEQUENCE: 64
tcctgcaccc acttcttctt g       21

<210> SEQ ID NO 65
<211> LENGTH: 21
<212> TYPE: DNA
<213> ORGANISM: Artificial Sequence
<220> FEATURE:
<223> OTHER INFORMATION: PCR Primer

<400> SEQUENCE: 65
ccaaactggg caaggagatc t       21

<210> SEQ ID NO 66
<211> LENGTH: 24
<212> TYPE: DNA
<213> ORGANISM: Artificial Sequence
<220> FEATURE:
<223> OTHER INFORMATION: PCR Primer

<400> SEQUENCE: 66
ggcccaggtg tttcatataa ttct       24

<210> SEQ ID NO 67
<211> LENGTH: 27
<212> TYPE: DNA
<213> ORGANISM: Artificial Sequence
<220> FEATURE:
<223> OTHER INFORMATION: PCR Primer

<400> SEQUENCE: 67
tgcttcacct acactaccta caagatc       27

<210> SEQ ID NO 68
<211> LENGTH: 18
<212> TYPE: DNA
<213> ORGANISM: Artificial Sequence
<220> FEATURE:
<223> OTHER INFORMATION: PCR Primer

<400> SEQUENCE: 68
gacaattccg ggcttgga       18

<210> SEQ ID NO 69
<211> LENGTH: 27
<212> TYPE: DNA
<213> ORGANISM: Artificial Sequence
<220> FEATURE:
<223> OTHER INFORMATION: PCR Primer

<400> SEQUENCE: 69
cagattccac aaaagttcat agttgac       27

<210> SEQ ID NO 70
<211> LENGTH: 19
<212> TYPE: DNA
<213> ORGANISM: Artificial Sequence
<220> FEATURE:
<223> OTHER INFORMATION: PCR Primer

```
<400> SEQUENCE: 70
ccggcctctc ttggttagg                                              19

<210> SEQ ID NO 71
<211> LENGTH: 24
<212> TYPE: DNA
<213> ORGANISM: Artificial Sequence
<220> FEATURE:
<223> OTHER INFORMATION: PCR Primer

<400> SEQUENCE: 71
ctgctgtagt gttcaccaca ctga                                        24

<210> SEQ ID NO 72
<211> LENGTH: 24
<212> TYPE: DNA
<213> ORGANISM: Artificial Sequence
<220> FEATURE:
<223> OTHER INFORMATION: PCR Primer

<400> SEQUENCE: 72
ctgctgtagt gttcaccaca ctga                                        24

<210> SEQ ID NO 73
<211> LENGTH: 28
<212> TYPE: DNA
<213> ORGANISM: Artificial Sequence
<220> FEATURE:
<223> OTHER INFORMATION: PCR Primer

<400> SEQUENCE: 73
gatacacaga ccgtattctt catcctaa                                    28

<210> SEQ ID NO 74
<211> LENGTH: 26
<212> TYPE: DNA
<213> ORGANISM: Artificial Sequence
<220> FEATURE:
<223> OTHER INFORMATION: PCR Primer

<400> SEQUENCE: 74
tgaaagatga tagcattgat gtcaca                                      26

<210> SEQ ID NO 75
<211> LENGTH: 21
<212> TYPE: DNA
<213> ORGANISM: Artificial Sequence
<220> FEATURE:
<223> OTHER INFORMATION: PCR Primer

<400> SEQUENCE: 75
cgctctcagg cagagctatg t                                           21

<210> SEQ ID NO 76
<211> LENGTH: 21
<212> TYPE: DNA
<213> ORGANISM: Artificial Sequence
<220> FEATURE:
<223> OTHER INFORMATION: PCR Primer

<400> SEQUENCE: 76
cttgtccaga tgctgcatca g                                           21

<210> SEQ ID NO 77
```

```
<211> LENGTH: 19
<212> TYPE: DNA
<213> ORGANISM: Artificial Sequence
<220> FEATURE:
<223> OTHER INFORMATION: PCR Primer

<400> SEQUENCE: 77
gcgcgtggtg aaacacttc                                                   19

<210> SEQ ID NO 78
<211> LENGTH: 22
<212> TYPE: DNA
<213> ORGANISM: Artificial Sequence
<220> FEATURE:
<223> OTHER INFORMATION: PCR Primer

<400> SEQUENCE: 78
atcggcacag atctccttat cc                                               22

<210> SEQ ID NO 79
<211> LENGTH: 20
<212> TYPE: DNA
<213> ORGANISM: Artificial Sequence
<220> FEATURE:
<223> OTHER INFORMATION: PCR Primer

<400> SEQUENCE: 79
cgaagcatcc cgtgttcact                                                  20

<210> SEQ ID NO 80
<211> LENGTH: 18
<212> TYPE: DNA
<213> ORGANISM: Artificial Sequence
<220> FEATURE:
<223> OTHER INFORMATION: PCR Primer

<400> SEQUENCE: 80
gatgacaccc ggcttgga                                                    18

<210> SEQ ID NO 81
<211> LENGTH: 22
<212> TYPE: DNA
<213> ORGANISM: Artificial Sequence
<220> FEATURE:
<223> OTHER INFORMATION: PCR Primer

<400> SEQUENCE: 81
caggagtgat cttcaccacc aa                                               22

<210> SEQ ID NO 82
<211> LENGTH: 20
<212> TYPE: DNA
<213> ORGANISM: Artificial Sequence
<220> FEATURE:
<223> OTHER INFORMATION: PCR Primer

<400> SEQUENCE: 82
ggcgtccagg ttcttcatgt                                                  20

<210> SEQ ID NO 83
<211> LENGTH: 20
<212> TYPE: DNA
<213> ORGANISM: Artificial Sequence
<220> FEATURE:
<223> OTHER INFORMATION: PCR Primer

<400> SEQUENCE: 83
```
ggcgtccagg ttcttcatgt                                              20

<210> SEQ ID NO 84
<211> LENGTH: 23
<212> TYPE: DNA
<213> ORGANISM: Artificial Sequence
<220> FEATURE:
<223> OTHER INFORMATION: PCR Primer

<400> SEQUENCE: 84
gtagaatatc gcagcaggca gat                                          23

<210> SEQ ID NO 85
<211> LENGTH: 22
<212> TYPE: DNA
<213> ORGANISM: Artificial Sequence
<220> FEATURE:
<223> OTHER INFORMATION: PCR Primer

<400> SEQUENCE: 85
ctgcttccaa tacagccaca ag                                           22

<210> SEQ ID NO 86
<211> LENGTH: 24
<212> TYPE: DNA
<213> ORGANISM: Artificial Sequence
<220> FEATURE:
<223> OTHER INFORMATION: PCR Primer

<400> SEQUENCE: 86
gagcagctgt tactggtgaa ttca                                         24

<210> SEQ ID NO 87
<211> LENGTH: 19
<212> TYPE: DNA
<213> ORGANISM: Artificial Sequence
<220> FEATURE:
<223> OTHER INFORMATION: PCR Primer

<400> SEQUENCE: 87
cgtgcttcac ctggctcaa                                               19

<210> SEQ ID NO 88
<211> LENGTH: 21
<212> TYPE: DNA
<213> ORGANISM: Artificial Sequence
<220> FEATURE:
<223> OTHER INFORMATION: PCR Primer

<400> SEQUENCE: 88
ggtgctcaaa ccactgtgac a                                            21

<210> SEQ ID NO 89
<211> LENGTH: 22
<212> TYPE: DNA
<213> ORGANISM: Artificial Sequence
<220> FEATURE:
<223> OTHER INFORMATION: PCR Primer

<400> SEQUENCE: 89
ggaaatgttt gccacaggaa ga                                           22

<210> SEQ ID NO 90
<211> LENGTH: 21
<212> TYPE: DNA

```
<213> ORGANISM: Artificial Sequence
<220> FEATURE:
<223> OTHER INFORMATION: PCR Primer

<400> SEQUENCE: 90
tgtttcgtgt ttcccctgat g                                              21

<210> SEQ ID NO 91
<211> LENGTH: 16
<212> TYPE: DNA
<213> ORGANISM: Artificial Sequence
<220> FEATURE:
<223> OTHER INFORMATION: PCR Primer

<400> SEQUENCE: 91
ccactgcgcc caaacc                                                    16

<210> SEQ ID NO 92
<211> LENGTH: 20
<212> TYPE: DNA
<213> ORGANISM: Artificial Sequence
<220> FEATURE:
<223> OTHER INFORMATION: PCR Primer

<400> SEQUENCE: 92
gcaggattga ggcaagcttt                                                20

<210> SEQ ID NO 93
<211> LENGTH: 18
<212> TYPE: DNA
<213> ORGANISM: Artificial Sequence
<220> FEATURE:
<223> OTHER INFORMATION: PCR Primer

<400> SEQUENCE: 93
cccctggcca ctgaactg                                                  18

<210> SEQ ID NO 94
<211> LENGTH: 23
<212> TYPE: DNA
<213> ORGANISM: Artificial Sequence
<220> FEATURE:
<223> OTHER INFORMATION: PCR Primer

<400> SEQUENCE: 94
tggatgttct tgaggtgaat tcc                                            23

<210> SEQ ID NO 95
<211> LENGTH: 23
<212> TYPE: DNA
<213> ORGANISM: Artificial Sequence
<220> FEATURE:
<223> OTHER INFORMATION: PCR Primer

<400> SEQUENCE: 95
ggaattcacc tcaagaacat cca                                            23

<210> SEQ ID NO 96
<211> LENGTH: 21
<212> TYPE: DNA
<213> ORGANISM: Artificial Sequence
<220> FEATURE:
<223> OTHER INFORMATION: PCR Primer

<400> SEQUENCE: 96
gtggctatga cttcggtttg g                                              21
```

<210> SEQ ID NO 97
<211> LENGTH: 18
<212> TYPE: DNA
<213> ORGANISM: Artificial Sequence
<220> FEATURE:
<223> OTHER INFORMATION: PCR Primer

<400> SEQUENCE: 97
ccgtcccagg cacatcac                                                       18

<210> SEQ ID NO 98
<211> LENGTH: 18
<212> TYPE: DNA
<213> ORGANISM: Artificial Sequence
<220> FEATURE:
<223> OTHER INFORMATION: PCR Primer

<400> SEQUENCE: 98
ccgtcccagg cacatcac                                                       18

<210> SEQ ID NO 99
<211> LENGTH: 19
<212> TYPE: DNA
<213> ORGANISM: Artificial Sequence
<220> FEATURE:
<223> OTHER INFORMATION: PCR Primer

<400> SEQUENCE: 99
agagctgcgt tgcgtttgt                                                      19

<210> SEQ ID NO 100
<211> LENGTH: 22
<212> TYPE: DNA
<213> ORGANISM: Artificial Sequence
<220> FEATURE:
<223> OTHER INFORMATION: PCR Primer

<400> SEQUENCE: 100
tggcgaacac ttgcagatta ct                                                  22

<210> SEQ ID NO 101
<211> LENGTH: 20
<212> TYPE: DNA
<213> ORGANISM: Artificial Sequence
<220> FEATURE:
<223> OTHER INFORMATION: PCR Primer

<400> SEQUENCE: 101
cagagctgcg ttgcacttgt                                                     20

<210> SEQ ID NO 102
<211> LENGTH: 23
<212> TYPE: DNA
<213> ORGANISM: Artificial Sequence
<220> FEATURE:
<223> OTHER INFORMATION: PCR Primer

<400> SEQUENCE: 102
acacctgcag tttaccaatc gtt                                                 23

<210> SEQ ID NO 103
<211> LENGTH: 22
<212> TYPE: DNA
<213> ORGANISM: Artificial Sequence
<220> FEATURE:

<223> OTHER INFORMATION: PCR Primer

<400> SEQUENCE: 103
tctggaattc atcccaaaaa ca                                          22

<210> SEQ ID NO 104
<211> LENGTH: 22
<212> TYPE: DNA
<213> ORGANISM: Artificial Sequence
<220> FEATURE:
<223> OTHER INFORMATION: PCR Primer

<400> SEQUENCE: 104
tctggaattc atcccaaaaa ca                                          22

<210> SEQ ID NO 105
<211> LENGTH: 25
<212> TYPE: DNA
<213> ORGANISM: Artificial Sequence
<220> FEATURE:
<223> OTHER INFORMATION: PCR Primer

<400> SEQUENCE: 105
ccacctacaa tccttgaaag acctt                                       25

<210> SEQ ID NO 106
<211> LENGTH: 27
<212> TYPE: DNA
<213> ORGANISM: Artificial Sequence
<220> FEATURE:
<223> OTHER INFORMATION: PCR Primer

<400> SEQUENCE: 106
cagtgtagca atgatttcaa ttttctc                                     27

<210> SEQ ID NO 107
<211> LENGTH: 21
<212> TYPE: DNA
<213> ORGANISM: Artificial Sequence
<220> FEATURE:
<223> OTHER INFORMATION: PCR Primer

<400> SEQUENCE: 107
tccacgtgtt gagatcattg c                                           21

<210> SEQ ID NO 108
<211> LENGTH: 21
<212> TYPE: DNA
<213> ORGANISM: Artificial Sequence
<220> FEATURE:
<223> OTHER INFORMATION: PCR Primer

<400> SEQUENCE: 108
tcttgatggc cttcgattct g                                           21

<210> SEQ ID NO 109
<211> LENGTH: 19
<212> TYPE: DNA
<213> ORGANISM: Artificial Sequence
<220> FEATURE:
<223> OTHER INFORMATION: PCR Primer

<400> SEQUENCE: 109
cccacagcca ggacatcag                                              19

```
-continued
<210> SEQ ID NO 110
<211> LENGTH: 22
<212> TYPE: DNA
<213> ORGANISM: Artificial Sequence
<220> FEATURE:
<223> OTHER INFORMATION: PCR Primer

<400> SEQUENCE: 110
cttgcacagc acataggaaa gg                                              22
```